United States Patent
Shah et al.

(10) Patent No.: US 10,314,788 B2
(45) Date of Patent: *Jun. 11, 2019

(54) PHARMACEUTICAL COMPOSITIONS CONFIGURED TO DETER DOSAGE FORM SPLITTING

(75) Inventors: Manish S. Shah, Valley Cottage, NY (US); Ray J. Difalco, Valley Cottage, NY (US)

(73) Assignee: INSPIRION DELIVERY SCIENCES LLC, Basking Ridge, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/058,757

(22) PCT Filed: Feb. 12, 2009

(86) PCT No.: PCT/US2009/033919
§ 371 (c)(1),
(2), (4) Date: Mar. 31, 2011

(87) PCT Pub. No.: WO2010/019279
PCT Pub. Date: Feb. 18, 2010

(65) Prior Publication Data
US 2011/0184007 A1 Jul. 28, 2011

Related U.S. Application Data

(63) Continuation-in-part of application No. PCT/US2008/072914, filed on Aug. 12, 2008.
(Continued)

(51) Int. Cl.
| | | |
|---|---|---|
| *A61K 31/485* | (2006.01) | |
| *A61P 25/04* | (2006.01) | |
| *A61K 9/20* | (2006.01) | |
| *A61K 9/24* | (2006.01) | |
| *A61K 9/28* | (2006.01) | |
| *A61K 9/48* | (2006.01) | |
| *A61K 9/16* | (2006.01) | |
| *A61K 9/50* | (2006.01) | |
| *A61K 47/32* | (2006.01) | |

(Continued)

(52) U.S. Cl.
CPC .............. *A61K 9/2086* (2013.01); *A61K 9/16* (2013.01); *A61K 9/1617* (2013.01); *A61K 9/1623* (2013.01); *A61K 9/1641* (2013.01); *A61K 9/1652* (2013.01); *A61K 9/1676* (2013.01); *A61K 9/209* (2013.01); *A61K 9/2013* (2013.01); *A61K 9/2018* (2013.01); *A61K 9/2027* (2013.01); *A61K 9/2031* (2013.01); *A61K 9/2054* (2013.01); *A61K 9/2081* (2013.01); *A61K 9/28* (2013.01); *A61K 9/2846* (2013.01); *A61K 9/2886* (2013.01); *A61K 9/4808* (2013.01); *A61K 9/4858* (2013.01); *A61K 9/4866* (2013.01); *A61K 9/4891* (2013.01); *A61K 9/5026* (2013.01); *A61K 9/5031* (2013.01); *A61K 9/5042* (2013.01); *A61K 9/5047* (2013.01); *A61K 9/5078* (2013.01); *A61K 31/138* (2013.01); *A61K 31/437* (2013.01); *A61K 31/4458* (2013.01); *A61K 31/485* (2013.01); *A61K 47/32* (2013.01); *A61K 47/34* (2013.01); *A61K 47/38* (2013.01); *Y10T 156/10* (2015.01)

(58) Field of Classification Search
None
See application file for complete search history.

(56) References Cited

U.S. PATENT DOCUMENTS

| | | |
|---|---|---|
| 5,206,030 A | 4/1993 | Wheatley |
| 5,395,626 A | 3/1995 | Kotwal |

(Continued)

FOREIGN PATENT DOCUMENTS

| | | |
|---|---|---|
| FR | 2787715 A1 | 6/2000 |
| WO | WO 95/20947 A1 | 8/1995 |

(Continued)

OTHER PUBLICATIONS

Meijerman et al., "Herb-Drug Interactions in Oncology: Focus on Mechanisms of Induction", The Oncologist 2006; 11:742-752, Table 3, p. 743, col. 1, para 3, pp. 743, col. 2, para 1-3.
Avinza ("Extended release morphine sulfate" marketed by Ligand Phrmaceuticals Inc., hereinafter "Avinza"), cited in 2013.
Evonik et al., "EUDRAGIT RS PO" accessed at http://eudragit.evonik.com/product/eudrafit/en/products-services/eudragit-products/sustained-release-forn 2003.
Fisher et al., Roxicodone. A Chronic Pain Management Manual, Writers Club Press, IUniverse, Lincoln, NE (2002) Appx. E.
Guidance for Industry Dissolution Testing of Immediate Release Solid Oral Dosage Forms (hereinafter "FDA Guidance"), cited in 2013.
(Continued)

*Primary Examiner* — Robert A Wax
*Assistant Examiner* — Danah Al-Awadi
(74) *Attorney, Agent, or Firm* — Arent Fox LLP

(57) ABSTRACT

An oral pharmaceutical composition comprising a drug and one or more pharmaceutically acceptable excipients in a monolithic dosage form, wherein the dosage form is configured such that when the dosage form is divided into more than one piece and at least one of the pieces is administered to a subject the Cmax, AUC, and/or rate of drug released after administration is substantially the same or lower and the Tmax is higher than the Cmax, AUC, rate of drug released, and/or Tmax after administration of: (1) a comparable composition in intact dosage form of equal drug dosage of the administered at least one piece; (2) a bioequivalent drug composition in an intact dosage form of equal drug dosage to the administered at least one piece; and (3) a divided piece of a bioequivalent drug composition, wherein the divided piece comprises a drug dosage equal to the dosage of the administered piece of the oral composition. Methods of making the same and methods of using the same are also provided.

138 Claims, 1 Drawing Sheet

Related U.S. Application Data

(60) Provisional application No. 60/955,584, filed on Aug. 13, 2007.

(51) Int. Cl.
*A61K 47/34* (2017.01)
*A61K 47/38* (2006.01)
*A61K 31/138* (2006.01)
*A61K 31/437* (2006.01)
*A61K 31/4458* (2006.01)

(56) References Cited

U.S. PATENT DOCUMENTS

| | | | |
|---|---|---|---|
| 6,310,072 | B1 | 10/2001 | Smith |
| 6,419,954 | B1* | 7/2002 | Chu et al. ............ 424/465 |
| 6,911,217 | B1 | 6/2005 | Gren |
| 2003/0068371 | A1 | 4/2003 | Oshlack |
| 2003/0092724 | A1 | 5/2003 | Kao |
| 2003/0118641 | A1 | 6/2003 | Maloney |
| 2003/0185888 | A1* | 10/2003 | Wong .......... A61K 9/0004 424/473 |
| 2004/0052731 | A1 | 3/2004 | Hirsch |
| 2004/0131552 | A1 | 7/2004 | Boehm |
| 2005/0080012 | A1 | 4/2005 | Mickle |
| 2005/0163843 | A1 | 7/2005 | Boehm et al. |
| 2005/0176646 | A1 | 8/2005 | Mickle |
| 2005/0214223 | A1 | 9/2005 | Bartholomaeus et al. |
| 2005/0220715 | A1 | 10/2005 | Lin |
| 2005/0245483 | A1* | 11/2005 | Brogmann et al. ........ 514/57 |
| 2005/0266072 | A1* | 12/2005 | Oshlack et al. ........ 424/464 |
| 2005/0266080 | A1 | 12/2005 | Desai |
| 2005/0281748 | A1* | 12/2005 | Hirsh et al. ........... 424/10.1 |
| 2006/0014697 | A1 | 1/2006 | Mickle |
| 2006/0104909 | A1 | 5/2006 | Vaghefi |
| 2006/0110327 | A1 | 5/2006 | Emigh |
| 2006/0165602 | A1 | 7/2006 | Galer |
| 2007/0020339 | A1* | 1/2007 | Bear ................. 424/490 |
| 2007/0259045 | A1 | 11/2007 | Mannion |
| 2007/0269505 | A1 | 11/2007 | Flath |
| 2008/0085305 | A1 | 4/2008 | Baichwal |
| 2010/0099696 | A1 | 4/2010 | Soscia |

FOREIGN PATENT DOCUMENTS

| | | |
|---|---|---|
| WO | WO 95/25506 A1 | 9/1995 |
| WO | WO 00/027364 A1 | 5/2000 |
| WO | WO 03/013479 | 2/2003 |
| WO | WO2005117841 | 12/2005 |

OTHER PUBLICATIONS

Kral et al., Oxycodone Safety Handout for Patients (2007) accessed at www.Pain-Topics.org on May 7, 2013.

Opadry (Colorcon, accessed at http://www.colorcom.com/products/coatings/immediate-release/Opadry, accessed in 2013.

Opana ER (Oxymorphone Hydrochloride Extended-Release Tablets marketed by Endo Pharmaceuticals, Inc., accessed at heep://dailymed.nlm.nih.gov/dailymed/lookup.cfm?setid=545cea18-11ad-4881-b184-6f8bcc7908e4 accessed on Feb. 22, 2013.

Roxicodone Package Insert (Xanodyne (2009) accessed at http:dailymed.nlm.nih.gov/dailymed/archives/fdaDrugInfo.cfm?archiveid+12847 on May 7, 2013.

"Substrate"—Chambers $21^{st}$ Century Dictionary, London: Chambers Harrap, 2001, Credo Reference. Jan. 1, 2002, Web. Jul. 30, 2013 (www.credoreference.com/entry/chambdict/substrate).

Chithaluru et al. Asian Journal of Pharmaceutical and Clinical Research, 2011, 4:18-22.

Babak et al. Colloids and Surfaces B: Biointerfaces, 2007, 59:194-207.

Abbaspour et al. International Journal of Pharmaceutics, 2005, 303:88-94.

Murtaza, Acta Poloniae Pharmaceutica—Drug Research, 2012, 69:11-22.

Cozzolino et al., Colloids and Surfaces A: Physicochemical and Engineering Aspects, 2012, 403:45-53.

* cited by examiner

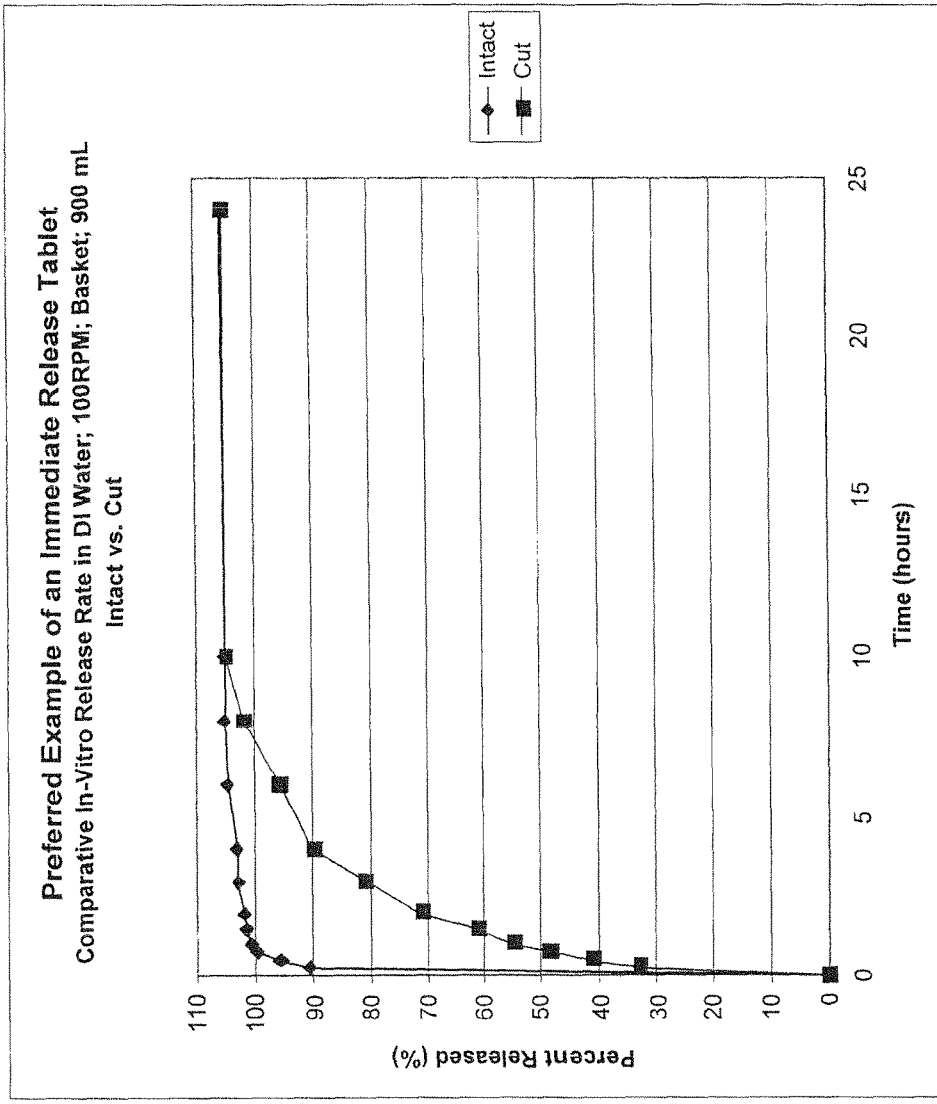

PHARMACEUTICAL COMPOSITIONS CONFIGURED TO DETER DOSAGE FORM SPLITTING

This application claims priority to PCT Application No. PCT/US2009/033919, filed Feb. 12, 2009, which is a Continuation-in-Part of PCT/US2008/072914, filed Aug. 12, 2018, which claims priority to U.S. Provisional Patent Application No. 60/955,584, filed Aug. 13, 2017, which is incorporated herein by reference in its entirety.

BACKGROUND OF THE INVENTION

The present invention is generally in the field of pharmaceutical compositions, and specifically relates to compositions that are designed to deter dosage form splitting and prevent improper administration of medications and adverse effects resulting from administration of inadequate or therapeutically inappropriate doses of a medication, immediately (i.e., in a single dose) and over time (i.e., with multiple doses). The present invention can comprise any drug. More specifically, it pertains to any drug of which patients could benefit from accurate dosage administration. It is also particularly useful to minimize the risk of medication overdose or suboptimal therapy, and adverse effects from excessive drug levels or from ineffective treatment of conditions due to inadequate blood concentrations of a medication.

In particular, the present invention relates to a pharmaceutical composition configured to deter dosage form splitting and use of such a composition in a dosage form to treat diseases or conditions while minimizing the risk of adverse effects from improper or irregular concentrations of drug in the blood due to dosage form splitting.

Dosage form splitting, also sometimes called tablet splitting or pill splitting, refers to the practice of modifying a dosage form to obtain a lower dose of an active ingredient, or to obtain multiple smaller doses by dividing the dosage form into multiple pieces. Dosage form splitting typically involves oral dosage forms such as tablets or caplets, but can involve any monolithic pharmaceutical dosage forms. Dosage form splitting is accomplished typically by cutting or chopping the dosage form, but it can be accomplished by any means which allow the dosage form to be divided into multiple pieces. For example, the dosage form can be cut or chopped into multiple pieces with a sharp object such as a knife, split into pieces by breaking the dosage form with one's hands or even biting down on the dosage form with one's teeth. Dosage form splitting is often accomplished by means of a tablet splitter or pill splitter, which is a device comprising a means for holding the dosage form in place, and a blade which is pressed down to spit the dosage form.

In some cases, dosage forms are meant to be split and are scored so that a patient can easily divide the dosage form into multiple pieces. However, for many medications, it is unsafe to split a dosage form. Unless scored to facilitate splitting, split dosage forms are typically uneven and the amount per dose can vary dramatically. Some pharmaceutical compositions are extremely hard and require significant force to split. Other compositions are soft and crumble into a powder when split.

Variations in a patient's blood levels resulting from inconsistent dosages can result in adverse effects, such as suboptimal treatment of conditions or the buildup of toxic drug levels due to excessive doses of drug in the split dosage forms. Some medications require precise and consistent doses, such as cardiac medications or hormones. For example, patients taking anticoagulants such as warfarin, or hormones such as lexothyroxine, benefit from consistent, accurate dosages of the drugs.

It is an object of the present invention to provide a pharmaceutical composition that significantly reduces the potential for improper administration of medication and adverse effects resulting from administration of inadequate or therapeutically inappropriate doses of medication.

SUMMARY OF THE INVENTION

The present invention relates to an oral pharmaceutical composition, comprising a drug and one or more pharmaceutically acceptable excipients in a monolithic dosage form, wherein the dosage form is configured such that when the dosage form is divided into more than one piece and at least one of the pieces is administered to a subject, the Cmax and/or AUC achieved after a time period selected from the group consisting of 30 minutes, 1 hour, 2 hours, 4 hours, 8 hours, 12 hours, 16 hours, and 24 hours after administration is substantially the same or lower, preferably lower, more preferably at least about 20% lower, than the Cmax and/or AUC achieved after administration, and after the same selected time period, of a comparable composition in an intact dosage form of equal drug dosage of the administered at least one piece. "Substantially the same" means within 30%, preferably within 20%, and more preferably within 10%.

The present invention also relates to an oral pharmaceutical composition, comprising a drug and one or more pharmaceutically acceptable excipients in a monolithic dosage form, wherein the dosage form is configured such that when the dosage form is divided into more than one piece and at least one of the pieces is administered to a subject, the rate of drug released from the dosage form within a time period selected from the group consisting of 30 minutes, 1 hour, 2 hours, 4 hours, 8 hours, 12 hours, 16 hours, and 24 hours after administration is substantially the same or lower, preferably lower, more preferably at least about 20% lower, than the rate of drug released, after the same selected time period, from a comparable composition in an intact dosage form of equal drug dosage of the administered at least one piece.

The present invention also relates to an oral pharmaceutical composition, comprising a drug and one or more pharmaceutically acceptable excipients in a monolithic dosage form, wherein the dosage form is configured such that when the dosage form is divided into more than one piece and at least one of the pieces is administered to a subject, the Tmax achieved after administration is greater, preferably at least about 20% greater, than the Tmax achieved after administration of a comparable composition in an intact dosage form of equal drug dosage of the administered at least one piece.

The present invention also relates to an oral pharmaceutical composition, comprising a drug and one or more pharmaceutically acceptable excipients in a monolithic dosage form, wherein the dosage form is configured such that when the dosage form is divided into more than one piece and at least one of the pieces is administered to a subject, the Cmax and/or AUC achieved after a time period selected from the group consisting of 30 minutes, 1 hour, 2 hours, 4 hours, 8 hours, 12 hours, 16 hours, and 24 hours after administration is substantially the same or lower, preferably lower, more preferably at least about 20% lower, than the Cmax and/or AUC achieved after administration, and after the same selected time period, of an intact dosage form of a bioequivalent drug composition, wherein the drug dosage in the intact dosage form of the bioequivalent drug composition is equal to the drug dosage of the administered at least one piece.

The present invention also relates to an oral pharmaceutical composition, comprising a drug and one or more pharmaceutically acceptable excipients in a monolithic dosage form, wherein the dosage form is configured such that when the dosage form is divided into more than one piece and at least one of the pieces is administered to a subject, the rate of drug released from the dosage form within a time period selected from the group consisting of 30 minutes, 1 hour, 2 hours, 4 hours, 8 hours, 12 hours, 16 hours, and 24 hours after administration is substantially the same or lower, preferably lower, more preferably at least about 20% lower, than the rate of drug released, after the same selected time period, from an intact dosage form of a bioequivalent drug composition, wherein the drug dosage in the intact dosage form of the bioequivalent drug composition is equal to the drug dosage of the administered at least one piece.

The present invention also relates to an oral pharmaceutical composition, comprising a drug and one or more pharmaceutically acceptable excipients in a monolithic dosage form, wherein the dosage form is configured such that when the dosage form is divided into more than one piece and at least one of the pieces is administered to a subject, the Tmax achieved after administration is substantially the same or greater, preferably greater, more preferably at least about 20% greater, than the Tmax achieved administration of an intact dosage form of a bioequivalent drug composition, wherein the drug dosage in the intact dosage form of the bioequivalent drug composition is equal to the drug dosage of the administered at least one piece.

The present invention also relates to an oral pharmaceutical composition, comprising a drug and one or more pharmaceutically acceptable excipients in a monolithic dosage form, wherein the dosage form is configured such that when the dosage form is divided into more than one piece and at least one of the pieces is administered to a subject, the Cmax and/or AUC achieved after a time period selected from the group consisting of 30 minutes, 1 hour, 2 hours, 4 hours, 8 hours, 12 hours, 16 hours, and 24 hours after administration is substantially the same or lower, preferably lower, more preferably at least about 20% lower, than the Cmax and/or AUC achieved after administration, and after the same selected time period, of a divided piece of a bioequivalent drug composition, wherein the divided piece of the bioequivalent drug composition comprises a drug dosage equal to the drug dosage of the administered at least one piece.

The present invention also relates to an oral pharmaceutical composition, comprising a drug and one or more pharmaceutically acceptable excipients in a monolithic dosage form, wherein the dosage form is configured such that when the dosage form is divided into more than one piece and at least one of the pieces is administered to a subject, the rate of drug released from the dosage form within a time period selected from the group consisting of 30 minutes, 1 hour, 2 hours, 4 hours, 8 hours, 12 hours, 16 hours, and 24 hours after administration is substantially the same or lower, preferably at least about 20% lower, than the rate of drug released, after the same selected time period, from a divided piece of a bioequivalent drug composition, wherein the divided piece of the bioequivalent drug composition comprises a drug dosage equal to the drug dosage of the administered at least one piece.

The present invention also relates to an oral pharmaceutical composition, comprising a drug and one or more pharmaceutically acceptable excipients in a monolithic dosage form, wherein the dosage form is configured such that when the dosage form is divided into more than one piece and at least one of the pieces is administered to a subject, the Tmax achieved after administration is substantially the same or greater, preferably greater, more preferably at least about 20% greater, than the Tmax achieved after administration of a divided piece of a bioequivalent drug composition, wherein the divided piece of the bioequivalent drug composition comprises a drug dosage equal to the drug dosage of the administered at least one piece.

Preferably an oral pharmaceutical composition suitable for any of the above embodiments, and thus configured to deter dosage form splitting, comprises a barrier layer, comprising a first polymer; and a diffusion layer, comprising a second polymer, substantially covering the barrier layer, wherein the diffusion layer is bonded to the barrier layer and comprises a drug that is substantially homogeneously distributed within the second polymer and diffuses from the diffusion layer within the gastrointestinal (GI) tract. The pharmaceutical composition may optionally comprise an expansion layer comprising an expandable polymer and wherein the barrier layer substantially covers the expansion layer.

The present invention also relates to a method of treating a condition, comprising administering to a patient in need thereof a pharmaceutical composition of the invention.

BRIEF DESCRIPTION OF THE DRAWINGS

FIG. 1 is a graph of percent release rate versus time of a tablet made according to Example 1 when taken properly (intact) as compared to a "cut form" of the same tablet formulation.

DESCRIPTION OF THE PREFERRED EMBODIMENTS

The present invention provides the necessary amount of a drug to the patient to accomplish the pharmaceutical effect, while decreasing the potential for inaccurate dosing of medications and adverse effects resulting from administration of dosages of medication that are higher or lower than intended. Any drug of which patients could benefit from accurate dosage administration is suitable for use with the present invention.

The oral pharmaceutical composition of the invention can retard the release of the drug substance from a dosage form when the physical integrity of the dosage form containing the composition is compromised, and the resulting formulation is subsequently administered. A composition is "intact" if it is in a single, undivided, whole, monolithic dosage form, such that the physical structure of the composition has not been physically altered, changed, or modified from the original form. The composition is "physically compromised" or "divided" when it is in a form other than an intact form. This can be achieved by various means such as by splitting, cutting, chopping, or otherwise dividing a dosage form into more than one piece. The composition of the invention thus provides a deterrent to administration of physically compromised or divided dosage forms, as the drug will not be released at an appropriate rate from the formulation and as the actual amount of drug release can be decreased as compared to a comparable composition in an intact dosage form of equal drug dosage of the administered piece(s), or as compared to an intact or divided bioequivalent drug composition of equal drug dosage of the administered piece(s).

When administered as directed in intact, undivided form, the drug substance is released at a therapeutically appropriate rate from the composition within the gastrointestinal (GI) tract, preferably by dissolution and/or diffusion mechanisms. When administered in a divided dosage form, the full amount of drug may not be released, and the rate of release of the drug can be decreased in a therapeutically inappropriate manner.

According to one embodiment, the oral pharmaceutical composition of the present invention comprises: a barrier layer, comprising a first polymer; and a diffusion layer, comprising a second polymer, substantially covering the barrier layer, wherein the diffusion layer is bonded to the barrier layer and comprises a drug that is substantially homogeneously distributed within the second polymer and diffuses from the diffusion layer within the gastrointestinal tract. The pharmaceutical composition optionally comprises an expansion layer comprising an expandable polymer. In embodiments wherein the pharmaceutical composition comprises an expansion layer, the barrier layer substantially covers the expansion layer. Such a formulation is described, for example, in PCT Application No. PCT/US2008/072914, which is incorporated herein by reference in its entirety.

The oral pharmaceutical composition of the invention can comprise either or both extended release formulations, with a typical in vivo or in vitro slow release of drug over a period of about 6 to about 24 hours, preferably at least 80% of the drug released at about 12 to about 24 hours, as well as immediate release formulations, preferably with a release of at least 80%, more preferably at least 90% and most preferably at least 95%, of the drug in one hour, designed for oral administration.

The oral pharmaceutical composition can be in any pharmaceutical dosage form, preferably a monolithic dosage form. A monolithic dosage form is defined as a solid dosage form that is typically administered as a single piece. Monolithic dosage forms include, but are not limited to, tablets, coated tablets, caplets, lollipops, lozenges, troches, and pastilles. In preferred embodiments, the monolithic dosage form is a tablet.

In embodiments where the oral pharmaceutical composition comprises the optional expansion layer, the expansion layer is the innermost of the three layers of the drug composition. The expansion layer is preferably an inert layer, which does not contain any drug, and it comprises an expandable polymer. The expansion layer preferably has a thickness of about 0.5 to 15 mm, more preferably about 2 to 12 mm, and most preferably about 4 to 10 mm. The thickness of the expansion layer is preferably about 5 to 95%, more preferably about 40% to 95%, and most preferably about 50% to 90% of the thickness of the tablet.

In some embodiments, when the expandable polymer of the optional expansion layer is exposed to liquids, preferably liquids comprising water and/or an alcohol such as ethyl alcohol, the expandable polymer absorbs the liquid, and preferably expands and/or forms a gel. It is preferably a hydrophilic polymer, most preferably a hydrophilic polymer that swells upon contact with liquids and/or gels. In a preferred form, when the expansion layer is exposed to a liquid after the oral pharmaceutical composition is physically compromised and fragments of the composition containing the expansion layer are formed, the expandable polymer absorbs at least a portion of the liquid and forms a gel. Preferably the gel further retards release of the drug from the diffusion layer. The expansion layer preferably comprises a polymer present in the range of 5 to 90% by weight, based on the total weight of the dosage form.

Typical agents employed in the expansion layer include, but are not limited to pharmaceutically acceptable excipients such as methylcellulose, sodium carboxymethylcellulose, methylhydroxyethylcellulose, methylhydroxypropylcellulose, alginic acid, polyacrylic acid, and tragacanth, or a combination of two or more of these substances. Most preferred are hydroxypropyl methylcellulose, which is sometimes marketed under the tradename METHOCEL® and polyacrylic acid, which is sometimes marketed under the tradename CARBOPOL®.

The expansion layer may also include a disintegrant such as croscarmellose sodium or sodium starch glycolate, to help assure the expansion layer quickly disperses in a liquid. Additional ingredients which may be present in the expansion layer include, but are not limited to fillers, dyes, lubricants or water permeation enhancers such as sodium chloride. The use of highly soluble polymers, disintegrants or combinations thereof is generally known in the pharmaceutical arts, and as would be understood to one skilled in the art, any suitable highly soluble polymer or disintegrant or equivalent substances may be used in conjunction with the present invention and embodiments thereof.

The barrier layer is interior to the diffusion layer. In some embodiments wherein the pharmaceutical composition comprises an expansion layer, the expansion layer is the innermost of the three layers and the barrier layer substantially covers the expansion layer. Substantial covering of the expansion layer means that more that 80%, more preferably more than 90%, and most preferably more than 95% of the expansion layer is covered by the barrier layer. 100% coverage is most suitable. One or more barrier layers may be present in the oral pharmaceutical composition.

The barrier layer preferably has a thickness of about 0.1 to 2.5 mm, more preferably about 0.2 to 2.0 mm, and most preferably about 0.5 to 1.5 mm. The thickness of the barrier layer is preferably about 5 to 50%, more preferably about 8 to 30%, and most preferably about 10 to 25% of the total thickness of the composition.

The barrier layer serves a number of functions. For example, the barrier layer acts as barrier between the diffusion layer and the expansion layer, decreasing the amount of liquid that can enter into the expansion layer when the dosage form is in an intact form. Further, the barrier layer acts to improve the mechanical strength of the composition.

The barrier layer comprises a polymer. Typical barrier layer polymers include, but are not limited to, polyacrylates and the copolymers thereof (such as those marked under the tradename EUDRAGIT® NE 30 D), EUDRAGIT® FS 30 D, EUDRAGIT® RS 30 D, SURELEASE® from COLORCON®, AQUACOAT® from FMC®, and mixtures of EUDRAGIT® NE 30 D and AQUACOAT®, polyethylene glycol, polyethylene oxides, polyethylenes, polypropylenes, polyvinyl chlorides, polycarbonates, polystyrenes, and the like. The preferred polymers of the barrier layer are polyacrylate and polyethylene glycol and in particular, a polyacrylate dispersion. In embodiments wherein the pharmaceutical composition comprises an expansion layer, the barrier layer may also contain an adhesion agent to help it adhere to the expansion layer. The use of polymers resistant to biodegradation, adhesion agents or combinations thereof is generally known in the pharmaceutical arts, and as would be understood to one skilled in the art, any suitable bioresistant polymer or adhesion enhancing agent may be used in conjunction with the present invention and embodiments thereof.

Preferably, when a dosage form containing the oral pharmaceutical composition of the present invention is administered to a subject in the intact, undivided form, the barrier layer polymer does not substantially dissolve in the GI tract, mucous membranes, blood vessels or lungs. Rather, the barrier layer polymer passes through the body in a substantially undissolved form. "Substantially undissolved" means that less than 30%, more preferably less than 20% and most preferably less than 10% of the polymer is dissolved.

The diffusion layer substantially covers the barrier layer. Substantial covering of the barrier layer means that more that 80%, more preferably more than 90%, and most preferably more than 95% of the expansion layer is covered by the barrier layer. 100% coverage is most suitable.

The diffusion layer comprises a polymer and a drug, preferably a drug which is substantially homogeneously distributed in the polymer. "Substantially homogeneously distributed" means that more that 80%, more preferably more than 90%, and most preferably more than 95% of the drug is homogeneously distributed. The polymer and drug dispersion of the diffusion layer is applied and bonded to the barrier layer.

The diffusion layer preferably is a thin layer with a large surface area relative to the thickness of the layer. The diffusion layer preferably has a thickness of about 0.1 to 1.0 mm, more preferably about 0.15 to 0.7 mm, and most preferably about 0.2 to 0.4 mm. The thickness of the diffusion layer is preferably about 1 to 30%, more preferably about 2 to 20%, and most preferably about 3 to 10% of the thickness of the tablet. In the preferred embodiments of this invention, the diffusion layer is relatively thin as compared to the surface area of the diffusion layer.

In some preferred embodiments, one or more of the layers can contain dye which, when in contact with liquid or mouth saliva, will produce a stain or color. Examples of dyes include, but are not limited to, FD&C Red #3, FD&C Red #28 and FD&C Blue #1.

The drug incorporated in the pharmaceutical compositions of the invention can be any drug, or any combinations of two or more drugs. The drug or drugs in the pharmaceutical dosage form typically include any drug of which patients could benefit from accurate dosage administration. Accurate dosage refers to the intended dosage of drug or drugs for the patient, which should result in a therapeutic benefit, preferably with little or no adverse effects. In embodiments where the pharmaceutical composition comprises two or more drugs, the drugs can be intended to treat the same indication or different indications. In other embodiments where the pharmaceutical composition comprises two or more drugs, the one or more of the drugs can be incorporated to decrease the adverse effects of, or enhance the therapeutic effects of, one or more other drugs in the composition.

Examples of drugs that can be used with the present invention include, but are not limited to, the following types of drugs: analgesics, anti-inflammatory agents, anti-helminthics, anti-arrhythmic agents, anti-asthma agents, anti-bacterial agents, anti-viral agents, anti-coagulants, anti-depressants, anti-diabetics, anti-epileptics, anti-fungal agents, anti-gout agents, anti-hypertensive agents, anti-malarials, anti-migraine agents, anti-muscarinic agents, anti-neoplastic agents, immunosuppressants, anti-protozoal agents, anti-thyroid agents, anti-tussives, anxiolytics, sedatives, hypnotics, neuroleptics, beta-blockers, cardiac inotropic agents, cell adhesion inhibitors, corticosteroids, cytokine receptor activity modulators, diuretics, anti-parkinsonian agents, gastro-intestinal agents, histamine H-receptor antagonists, keratolytics, lipid regulating agents, muscle relaxants, nitrates and other anti-anginal agents, non-steroidal anti-asthma agents, nutritional agents, opioid analgesics, sex hormones, stimulants, vitamins, and anti-erectile dysfunction agents. However, any drug may be employed in the pharmaceutical composition, including nutraceuticals and other dietary supplements.

Preferred embodiments of the invention include one or more drugs selected from the class of drugs selected from the group consisting of: analgesic drugs such as opioids; cardiovascular drugs, such as anticoagulants, anti-diabetes drugs, HMG CoA reductase inhibitors, angiotensin-converting enzyme inhibitors, angiotensin receptor antagonists; and psychiatric medications such as antipsychotics, benzodiazepines, antidepressants, and sleep medications.

In addition to one or more drugs, the diffusion layer contains one or more polymers. Examples of polymers which can be used in the diffusion layer include, but are not limited to, ethyl cellulose, a quaternary ammonium acrylic or methacrylic polymers, an acrylic or a methacrylic ester copolymers or a mixture thereof, which can also be used as sustained release agents. Common tradenames include various grades of EUDRAGIT®s (all from Röhm), and SURELEASE® (from COLORCON®). The preferred polymers of the diffusion layer are acrylic or methacrylic polymers and particularly ethyl acrylate or methyl methylacrylate dispersions. The use of diffusion polymers, preferably gradually abrading polymers, is generally known in the pharmaceutical arts, and as would be understood to one skilled in the art, any suitable gradually abrading polymers or agent may be used in conjunction with the present invention and embodiments thereof.

Suitable waxes may replace a portion or all of the polymer in the diffusion layer. Suitable waxes include both synthetic and natural waxes, as well as wax-like substances, fats and fatty substances, hydrocarbons like paraffin, beeswax, carnauba wax, and the like, including combinations of these substances. These substances dissolve very slowly or not at all in the GI tract. The use of wax-like substances is generally known in the pharmaceutical arts, and as would be understood to one skilled in the art, any suitable wax-like substances may be used in conjunction with the present invention and embodiments thereof.

The diffusion layer may optionally also contain sustained or extended release and/or enteric coating. Examples of such materials are cellulose acetate phthalate, hydroxypropyl methylcellulose phthalate, polyvinyl acetate phthalate, methacrylic acid:acrylic ester copolymer, hydroxypropyl methylcellulose acetate succinate, shellac, cellulose acetate trimellitate, and mixtures thereof. The diffusion layer may also contain water-soluble polymers such as polyvinylpyrrolidone, hydroxypropyl cellulose, hydroxypropyl methylcellulose, polyethylene glycol having a molecular weight of from 1,700 to 20,000 and polyvinyl alcohol and monomers therefor and mixtures thereof. The use of sustained, extended and enteric coating materials is generally known in the pharmaceutical arts, and as would be understood to one skilled in the art, any suitable sustained, extended and enteric coating materials or similar agents may be used in conjunction with the present invention and embodiments thereof.

In the preferred embodiments, for the barrier as well as the diffusion layer, the acrylic coating is an acrylic lacquer used in the form of an aqueous dispersion that is commercially available from Röhm Pharma under the tradename EUDRAGIT®.

The substantially homogeneous distribution of drug within the polymer of the diffusion layer allows for the release of drug at a defined desired rate within the GI tract, for example, such that it slowly releases the drug. The diffusion layer may be an immediate release layer or an extended release layer. The diffusion layer preferably maintains the same release profile, preferably up to 24 hours, as conventional intact formulations, even when the layer is broken up into smaller pieces. The presence of the drug in the diffusion layer is thought to contribute to the formation of pores in the polymers of the diffusion layer. The presence of pores allows for the gradual erosion of the diffusion layer and release of the drug. The release rate of drug can be adjusted by changing the polymer pore size. For example, reduction in polymer pore size can reduce the release rate of the drug. Stretching or exposing the diffusion layer to solvents will also reduce polymer pore size and reduce the release rate of the drug.

The diffusion and barrier layers are bonded to each other. The layers may be bonded by any method known in the art. In some embodiments, the layers are chemically bonded, or preferably, they are physically bonded. In preferred embodiments, a physical bond is formed between layers by heat curing. In another preferred embodiment, the layers are in powder form and are physically bonded by using a tablet press. In some embodiments, the expansion and barrier layers may be manufactured as bulk tablets and stored for a period of time, preferably up to seven days, as long as the barrier layer is not cured.

Preferably, the composition is configured such that when the pharmaceutical composition is physically compromised or divided, and particles of the pharmaceutical composition containing the diffusion layer and the barrier layer are formed, the bond between the diffusion layer and barrier layer within the particles is substantially preserved. In the preferred embodiments of this invention, compromising the drug product in this manner will result in pieces of the diffusion layer and pieces of the barrier layer tightly bonded together within the particles resulting from the compromising activity. Thus, in the preferred embodiments of this invention, the relative surface area of the diffusion layer will increase only marginally (e.g., no more than 50%, preferably no more than 25%, most preferably no more than 10%), when particles are produced in a range of 500 mesh to 8 mesh. The control of drug diffusion surface area in the preferred embodiments of this invention prevents a rapid release of the drug product from the drug product components, even if compromised or divided.

The formation of a bond between the diffusion layer and the barrier layer is important in achieving deterrence of dosage form splitting because when the dosage forms of the invention are physically compromised, such as by cutting, chopping, splitting, or otherwise dividing, the barrier layer protects the inner side of the diffusion layer, preventing significant increase in drug release. Therefore, the drug substance maintains release gradually at substantially its designed rate from the outer side of the diffusion layer.

The layer bonding design feature may be optimized by applying the diffusion layer immediately after the barrier layer is applied and then curing them together.

The diffusion layer polymer is able to hold the drug within and thus prevent the dumping of drug substance after alteration of the dosage form. The barrier layer and optional expansion layer enhance the dosage form splitting deterrent feature of the pharmaceutical composition.

One or more other components, such as any pharmaceutically acceptable excipient, may be added to any or all of the various layers provided that they do not interfere with the drug and provide a desired benefit to the pharmaceutical. Exemplary of such other components are: plasticizers, anti-adhesive, inert fillers, lipophilic agents and pigments used in a known manner. Tackiness of the water-dispersible film forming substance may be overcome by simply incorporating an anti-adhesive in the coating. Examples of anti-adhesive are metallic stearates, microcrystalline cellulose, calcium phosphate, AEROSIL® 200, and talc. Those of ordinary skill in the art would understand the need for and applicability of such other components to overcome manufacturing, shelf-life or release profile issues.

Examples of plasticizers for use in accordance with the present invention include triacetin, acetylated monoglyceride, olive oil, acetyl tributyl citrate, acetyl triethyl citrate, glycerin, sorbitol, polyethylene glycol, and polypropyleneglycol.

Fillers/diluents/binders may be incorporated such as sucrose, sorbitol, mannitol, various grades of lactose, various grades of microcrystalline cellulose, dextrins, maltodextrins, starches or modified starches, sodium phosphate, calcium phosphate, calcium carbonate, gelatin, polyvinylpyrrolidone, and sodium carboxymethylcellulose.

Disintegrants may be used such as cellulose derivatives, including microcrystalline cellulose, low-substituted hydroxypropyl cellulose, croscarmellose sodium, alginic acid, insoluble polyvinylpyrrolidone, and sodium carboxymethyl starch.

Glidants and lubricants may be incorporated such as stearic acid, metallic stearates, talc, waxes, and glycerides with high melting temperatures, colloidal silica, sodium stearyl fumarate, polyethyleneglycols, and alkyl sulphates.

Surfactants may be employed such as non-ionic (various grades of polysorbate); anionic such as docusate sodium and sodium lauryl sulfate, and cationic such as benzalkonium chloride. An example of an amphoteric surfactant is 1,2-diacyl-L-phosphatidylcholine. The preferred surfactants are TWEEN® 80, BRIJ®, and Nanoxyl-100.

Other appropriate pharmaceutically acceptable excipients may include colorants, flavoring agents, pH adjusting agents, solubilizing agents, wetting agents, solvent resistant agents and buffering agents.

One or more other layers may be disposed under the expansion layer, or between the expansion layer and the barrier layer or above or on top of the diffusion layer. For example, in some embodiments, the expansion layer is not in direct contact with the barrier layer, as one or more layers may be disposed between the expansion layer and the barrier layer. In other embodiments, the expansion layer can cover another layer that is disposed under the expansion layer. In some embodiments, one or more additional release layers comprising one or more additional drugs can be on top of the diffusion layer. In some embodiments, the additional release layer can be an extended release layer or an immediate release layer. In some embodiments, both an extended release layer and an immediate release layer can be on top of the diffusion layer. The one or more additional drugs can be any drug, including drugs that may be part of the diffusion layer of the composition. Preferably, the layer on top of the diffusion layer is an immediate release layer, and drugs in the immediate release layer include any drug.

In some embodiments, the pharmaceutical composition is a dosage form in which one or more of the layers are difficult to physically compromise. For example, in some embodiments, the dosage form cannot be easily divided with by hand, knife or blade or other device. In preferred embodiments, the pharmaceutical composition is a tablet dosage form having a tablet hardness, preferably higher than 10 kp, more preferably higher than 20 kp, and most preferably between 10 kp and 50 kp.

Because of the described features above, the potential for patients to split the dosage forms, which contain a fraction of the dosage of the intact tablet, is decreased. For example, a patient seeking to cut an 80 mg tablet into four tablet pieces of a lower dose would be unable to achieve the necessary therapeutic effect with the cut tablet pieces, in comparison to a comparable composition of equal drug dosage of the administered piece in an intact dosage form. A "comparable composition in an intact dosage form of equal drug dosage of the administered at least one piece" refers to an intact, undivided pharmaceutical composition, such as a monolithic dosage form, which has the same drug(s), the same amount of the drug(s), and the same amount of other components such as pharmaceutically acceptable excipients, in the same weight ratio. In other words, the main difference between the compositions is that one is divided and the other is intact, however the constituents are the same. The patient may be unable to achieve the necessary therapeutic effect, because the tablet pieces would not release the same amount of drug, as compared to the amount of drug released in the comparable intact composition. The patient may experience sub-therapeutic levels of the drug, due for example to a reduction in Cmax and/or AUC, or a longer release of the drug, either through a decreased rate of release or an increased Tmax.

Preferably, when utilizing the preferred composition of the invention and administering properly in an intact form, the drug is released at a desired release rate from the diffusion layer, and the remainder of the pharmaceutical composition passes through the patient's body in an inert manner, because the barrier layer prevents the remainder of the composition from being broken down in the GI tract. The desired release rate may be the release rate typically obtained from the intended use, such as described in the prescribing information associated with a commercial drug product.

In a still preferred embodiment of the invention wherein the composition comprises an expansion layer, physically compromising the drug product results in the expansion layer being dispersed between particles containing diffusion layer and barrier layer components, as a component of the particles containing diffusion layer and barrier layer components, or both. Thus, in preferred embodiments of the invention, once exposed to bodily fluids or other liquids, the particles containing the diffusion layer and barrier layer components become embedded in the swelled expansion layer, such that the net diffusion of the drug substance into such bodily fluids or other liquids occurs at substantially lower rates than those observed from the diffusion out of the uncompromised drug product.

In preferred embodiments of the invention, the resulting pharmaceutical composition will have both a mechanism to control and largely maintain the rate of diffusion of the drug substance from the drug substance containing compartments of the composition, as well as a mechanism to retard diffusion of the drug substance from the drug-substance containing compartments of the composition and to retain a substantial proportion of the drug substance once the composition is compromised and exposed, in whole or in part, to a liquid. A benefit of the invention is that it may prevent "dose dumping" from administration of the cut pieces.

In preferred embodiments, compromised or divided pieces of the pharmaceutical composition of the present invention release a lower percentage of drug compared to a comparable composition in an intact dosage form of equal drug dosage of the administered piece(s).

The most relevant pharmacokinetic parameters for understanding the features and benefits of the invention are Cmax (maximum blood serum concentration of the drug substance and/or active metabolites), AUC (area under the serum concentration curve: the integral of the blood serum concentration of the drug substance and/or active metabolites over time) and Tmax (the time to reach Cmax).

In preferred embodiments, the oral pharmaceutical composition of the present invention, comprising a drug and one or more pharmaceutically acceptable excipients in a monolithic dosage form, is configured such that when the dosage form is divided into more than one piece and at least one of the pieces is administered to a subject, the Cmax and/or AUC achieved after a time period selected from the group consisting of 30 minutes, 1 hour, 2 hours, 4 hours, 8 hours, 12 hours, 16 hours, and 24 hours after administration is substantially the same or lower, preferably lower, than the Cmax and/or AUC achieved after administration, after the same time period, of a comparable composition in an intact dosage form of equal drug dosage of the administered at least one piece. In some embodiments, the Cmax and/or AUC are preferably at least about 10%, 20%, 30%, 40%, 50%, 60%, 70%, 80%, or 90% lower, and most preferably at least about 20%.

For example, if the pharmaceutical composition of the present invention is a tablet comprising 100 mg of a drug, and a subject divides the 100 mg tablet into 2 pieces each containing 50 mg and takes one of the divided tablet pieces, the Cmax and/or AUC achieved after administration of the divided tablet piece and after a selected time period would be substantially the same or preferably lower than the Cmax and/or AUC achieved after administration, after the same time period, of an intact, undivided 50 mg tablet having the same constituents. For example, if the AUC achieved 8 hours after administration of the comparable composition (in this case, an intact, undivided 50 mg tablet) was 200 ng/mL, the AUC achieved 8 hours after administration of the divided 50 mg piece would be substantially the same or lower than 200 ng/mL, and preferably lower than about 160 ng/mL (i.e., at lease 20% lower).

In some embodiments, the oral pharmaceutical composition of the present invention, comprising a drug and one or more pharmaceutically acceptable excipients in a monolithic dosage form, is configured such that when the dosage form is divided into more than one piece and at least one of the pieces is administered to a subject, the amount of drug released after a time period selected from the group consisting of 30 minutes, 1 hour, 2 hours, 4 hours, 8 hours, 12 hours, 16 hours, and 24 hours after administration is substantially the same or preferably lower than the amount of drug released after administration, after the same time period, of a comparable composition in an intact dosage form of equal drug dosage of the administered at least one piece. In some embodiments, the amount of drug released is preferably at least about 10%, 20%, 30%, 40%, 50%, 60%, 70%, 80%, or 90% lower, and most preferably at least about 20%.

In some embodiments, the oral pharmaceutical composition, comprising a drug and one or more pharmaceutically acceptable excipients in a monolithic dosage form, is configured such that when the dosage form is divided into more than one piece and at least one of the pieces is administered to a subject, the rate of drug released from the dosage form within a time period selected from the group consisting of 30 minutes, 1 hour, 2 hours, 4 hours, 8 hours, 12 hours, 16 hours, and 24 hours after administration is substantially the same or preferably lower than the rate of drug released, after the same time period, from a comparable composition in an intact dosage form of equal drug dosage of the administered at least one piece. In some embodiments, the rate of drug released is preferably at least about 10%, 20%, 30%, 40%, 50%, 60%, 70%, 80%, or 90% lower, and most preferably at least about 20%.

For example, if a comparable composition of equal drug dosage of the administered piece releases the drug at a rate of 5 mg/hr within 4 hours after administration, then the rate of drug released within 4 hours after administration of the divided tablet would be substantially the same or lower, preferably at a rate of at most 4 mg/hour (at least about 20% lower).

In some embodiments, the oral pharmaceutical composition, comprising a drug and one or more pharmaceutically acceptable excipients in a monolithic dosage form, is configured such that when the dosage form is divided into more than one piece and at least one of the pieces is administered to a subject, the Tmax achieved after administration is substantially the same or greater, preferably greater, than the Tmax achieved after administration of a comparable composition in an intact dosage form of equal drug dosage of the administered at least one piece. In some embodiments, the Tmax is preferably at least about 10%, 20%, 30%, 40%, 50%, 60%, 70%, 80%, or 90% greater, and most preferably at least about 20%.

For example, if the Tmax achieved 4 hours after administration of the comparable composition is 100 minutes, the Tmax achieved 4 hours after administration of a divided dosage form would be substantially the same or greater, preferably greater, than 100 minutes, and preferably greater than about 120 minutes (at least about 20% greater).

In some embodiments, the oral pharmaceutical composition, comprising a drug and one or more pharmaceutically acceptable excipients in a monolithic dosage form, is configured such that when the dosage form is divided into more than one piece and at least one of the pieces is administered to a subject, the Cmax and/or AUC achieved after a time period selected from the group consisting of 30 minutes, 1 hour, 2 hours, 4 hours, 8 hours, 12 hours, 16 hours, and 24 hours after administration is substantially the same or lower than the Cmax and/or AUC achieved after administration of an intact dosage form of a bioequivalent drug composition, wherein the drug dosage in the intact dosage form of the bioequivalent drug composition is equal to the drug dosage of the administered at least one piece. In some embodiments, the Cmax and/or AUC are preferably at least about 10%, 20%, 30%, 40%, 50%, 60%, 70%, 80%, or 90% lower, and most preferably at least about 20%.

A "bioequivalent drug composition" refers to a composition which contains the same amount of the same drug as the reference drug composition and, when each of the compositions is administered in intact form, has an AUC and Cmax within the range of 80 to 125% of the AUC and Cmax of the reference drug composition. A drug composition which is bioequivalent to the pharmaceutical composition of the present invention contains the same drug but does not employ a means for deterring dosage form splitting or does not employ the same means for deterring dosage form splitting as the pharmaceutical composition of the present invention. For example, a bioequivalent drug composition may not contain the same excipients in the same amounts and/or weight ratios as those in a reference drug composition. In some embodiments, the components in a bioequivalent drug composition may not be constituted in the same manner as the reference drug composition.

For example, if the pharmaceutical composition of the present invention is a tablet comprising 100 mg of a drug, and a subject divides the 100 mg into 2 pieces each containing 50 mg and takes one of the divided tablet pieces, the Cmax and/or AUC achieved after administration would be substantially the same or lower than the Cmax and/or AUC achieved after administration, after the same time period, of an intact dosage form of a bioequivalent drug composition, wherein the drug dosage in the intact dosage form of the bioequivalent drug composition is equal to the drug dosage of divided tablet piece. Therefore, in this example, the Cmax and/or AUC achieved after administration of the divided 50 mg tablet would be substantially the same or lower, preferably at least about 20% lower, than that achieved after administration of an intact, undivided, bioequivalent 50 mg tablet. For example, if the AUC achieved 8 hours after administration of the intact, undivided, bioequivalent 50 mg tablet was 200 ng/mL, then the AUC achieved 8 hours after administration of a divided 50 mg dosage form according to the invention would be substantially the same or lower than 200 ng/mL, and preferably lower than about 160 ng/mL (i.e., at least about 20% lower).

In some embodiments, the oral pharmaceutical composition, comprising a drug and one or more pharmaceutically acceptable excipients in a monolithic dosage form, is configured such that when the dosage form is divided into more than one piece and at least one of the pieces is administered to a subject, the amount of drug released from the dosage form within a time period selected from the group consisting of 30 minutes, 1 hour, 2 hours, 4 hours, 8 hours, 12 hours, 16 hours, and 24 hours after administration is substantially the same or lower than the amount of drug released, after the same time period, from an intact dosage form of a bioequivalent drug composition, wherein the drug dosage in the intact dosage form of the bioequivalent drug composition is equal to the drug dosage of the administered at least one piece. In some embodiments, the amount of drug released is preferably at least about 10%, 20%, 30%, 40%, 50%, 60%, 70%, 80%, or 90% lower, and most preferably at least about 20%.

In some embodiments, the oral pharmaceutical composition comprising a drug and one or more pharmaceutically acceptable excipients in a monolithic dosage form, is configured such that when the dosage form is divided into more than one piece and at least one of the pieces is administered to a subject, the rate of drug released from the dosage form within a time period selected from the group consisting of 30 minutes, 1 hour, 2 hours, 4 hours, 8 hours, 12 hours, 16 hours, and 24 hours after administration is substantially the same or lower than the rate of drug released, after the same time period, from an intact dosage form of a bioequivalent drug composition, wherein the drug dosage in the intact dosage form of the bioequivalent drug composition is equal to the drug dosage of the administered at least one piece. In some embodiments, the rate of drug released is preferably at least about 10%, 20%, 30%, 40%, 50%, 60%, 70%, 80%, or 90% lower, and most preferably at least about 20%.

In some embodiments, the oral pharmaceutical composition, comprising a drug and one or more pharmaceutically acceptable excipients in a monolithic dosage form, is configured such that when the dosage form is divided into more than one piece and at least one of the pieces is administered to a subject, the Tmax achieved after administration is substantially the same or greater, preferably greater, than the Tmax achieved administration of an intact dosage form of a bioequivalent drug composition, wherein the drug dosage in the intact dosage form of the bioequivalent drug composition is equal to the drug dosage of the administered at least one piece. In some embodiments, the Tmax is preferably at least about 10%, 20%, 30%, 40%, 50%, 60%, 70%, 80%, or 90% greater, and most preferably at least about 20%.

In some embodiments, the oral pharmaceutical composition, comprising a drug and one or more pharmaceutically acceptable excipients in a monolithic dosage form, is configured such that when the dosage form is divided into more than one piece and at least one of the pieces is administered to a subject, the Cmax and/or AUC achieved after a time period selected from the group consisting of 30 minutes, 1 hour, 2 hours, 4 hours, 8 hours, 12 hours, 16 hours, and 24 hours after administration is substantially the same or lower than the Cmax and/or AUC achieved after administration, after the same time period, of a divided piece of a bioequivalent drug composition, wherein the divided piece of the bioequivalent drug composition comprises a drug dosage equal to the drug dosage of the administered at least one piece. In some embodiments, the Cmax and/or AUC are preferably at least about 10%, 20%, 30%, 40%, 50%, 60%, 70%, 80%, or 90% lower, and most preferably at least about 20%.

The phrase "divided piece of a bioequivalent composition" refers to a piece of a monolithic dosage form which contains the same amount of the same drug as the reference drug composition and, when each of the compositions is administered in intact form, has an AUC and Cmax within the range of 80 to 125% of the AUC and Cmax of the reference drug composition. The divided piece of a bioequivalent composition has the same amount of the same drug, but different amounts of other components such as pharmaceutically acceptable excipients, compared to a divided piece of a reference drug composition, such as a composition of the presently claimed invention.

For example, if the pharmaceutical composition of the present invention is a tablet comprising 100 mg of a drug, and a subject divides the 100 mg tablet into 2 pieces each containing 50 mg and takes one of the divided tablet pieces, the Cmax and/or AUC achieved after administration would be substantially the same or lower than the Cmax and/or AUC achieved after administration, after the same time period, of a divided piece of a bioequivalent composition, which divided piece has a drug dosage equal to the drug dosage of the administered at least one piece according to the invention. Therefore, if the divided tablet pieces of the pharmaceutical composition of the present invention contained 50 mg of drug, the Cmax and/or AUC achieved after administration of the divided 50 mg tablet would be substantially the same or lower, preferably lower, more preferably at least about 20% lower, than a divided piece of a bioequivalent drug composition wherein the divided piece contains 50 mg of drug. For example, if the AUC achieved 8 hours after administration of a divided piece of a bioequivalent drug composition, comprising 50 mg, was 200 ng/mL, then the AUC achieved 8 hours after administration of a divided 50 mg dosage form of the pharmaceutical composition of the present invention would be substantially the same or lower than 200 ng/mL, and preferably lower than about 160 ng/mL (i.e., at least about 20% lower).

In some embodiments, the oral pharmaceutical composition, comprising a drug and one or more pharmaceutically acceptable excipients in a monolithic dosage form, is configured such that when the dosage form is divided into more than one piece and at least one of the pieces is administered to a subject, the amount of drug released from the dosage form within a time period selected from the group consisting of 30 minutes, 1 hour, 2 hours, 4 hours, 8 hours, 12 hours, 16 hours, and 24 hours after administration is substantially the same or lower than the amount of drug released from a divided piece of a bioequivalent drug composition, wherein the divided piece of the bioequivalent drug composition comprises a drug dosage equal to the drug dosage of the administered at least one piece. In some embodiments, the amount of drug released is preferably at least about 10%, 20%, 30%, 40%, 50%, 60%, 70%, 80%, or 90% lower, and most preferably at least about 20%.

In some embodiments, the oral pharmaceutical composition, comprising a drug and one or more pharmaceutically acceptable excipients in a monolithic dosage form, is configured such that when the dosage form is divided into more than one piece and at least one of the pieces is administered to a subject, the rate of drug released from the dosage form within a time period selected from the group consisting of 30 minutes, 1 hour, 2 hours, 4 hours, 8 hours, 12 hours, 16 hours, and 24 hours after administration is substantially the same or lower than the rate of drug released, after the same time period, from a divided piece of a bioequivalent drug composition, wherein the divided piece of the bioequivalent drug composition comprises a drug dosage equal to the drug dosage of the administered at least one piece. In some embodiments, the rate of drug released is preferably at least about 10%, 20%, 30%, 40%, 50%, 60%, 70%, 80%, or 90% lower, and most preferably at least about 20%.

In some embodiments, the oral pharmaceutical composition, comprising a drug and one or more pharmaceutically acceptable excipients in a monolithic dosage form, is configured such that when the dosage form is divided into more than one piece and at least one of the pieces is administered to a subject, the Tmax achieved after administration is substantially the same or greater, preferably greater, than the Tmax achieved after administration of a divided piece of a bioequivalent drug composition, wherein the divided piece of the bioequivalent drug composition comprises a drug dosage equal to the drug dosage of the administered at least one piece.

"Substantially the same" means within 30%, preferably within 20%, and more preferably within 10%.

The drug composition of the present invention is preferably independent of pH in its release profile. Further, there is preferably no significant change (preferably, less than 10% change) in the release rate of the formulation after 3 months of storage at 40° C. at 75% relative humidity, when measured by the USP basket method of U.S. Pharmacopoeia, with USP Apparatus I, at 100 rpm (basket) at 900 mL aqueous buffer at pH 1.6 and 7.2 and at 37° C.

All references cited herein are hereby incorporated by reference in their entirety.

The following examples are employed to demonstrate and illustrate the present invention.

Example 1

| Expansion layer | |
|---|---|
| Mannitol - | 70 mg |
| Microcrystalline Cellulose- | 50 mg |
| Carbopol 71G - | 128 mg |
| Hydroxypropyl Methylcellulose, type 2910 - | 128 mg |

| | |
|---|---|
| (METHOCEL ™ K4M CR) | |
| Croscarmellose sodium - | 20 mg |
| (AC-DI-SOL ®) | |
| Magnesium Stearate - | 4 mg |
| Barrier layer | |
| | |
| EUDRAGIT ® NE 30D solids - | 97.3 mg |
| Calcium Stearate - | 16.2 mg |
| Simethicone Emulsion - | 0.2 mg |
| Purified water- | — |
| Diffusion layer | |
| | |
| Oxycodone Hydrochloride - | 10 mg |
| EUDRAGIT ® NE 30D solids - | 32.4 mg |
| Aerosil ® 200 - | 2 mg |
| Tween ® 80 - | 2 mg |
| Purified water - | — |
| Color coat | |
| | |
| Opadry 85F18422 Powder - | 30 mg |
| Purified Water - | — |

Tablets comprising the pharmaceutical composition of Example 1 were cut into pieces using a sharp device such as a knife and scissors. FIG. 1 shows the comparison of such rate. This demonstrates that when the tablets of the current invention are physically compromised and cut, the physical bond between the diffusion layer and the barrier layer is substantially preserved. The relative surface area of the diffusion layer increases only marginally, preventing a significant increase in the drug release. Therefore, in some embodiments, even when the dosage form containing the pharmaceutical composition of the invention is physically compromised, the drug substance maintains essentially the same release profile, as compared to an intact dosage form.

Example 2

Doctor A, a health care professional, is treating Patient B, for a cardiac condition requiring treatment with extended release nifedipine. Doctor A repeatedly tells the patient that an extended release nifedipine dosage form that she had previously prescribed, which is not a pharmaceutical composition of the present invention, should not be split or divided into multiple pieces. Doctor A informs Patient B that dividing the dosage form could result in a "dumping" of the drug and that dangerously high levels of drug could be released in a short period of time. Doctor A is concerned about the adverse effects resulting from the dosage form splitting. To help the patient achieve optimal therapeutic benefits and a reduced potential for adverse effects, Doctor A prescribes to the patient a pharmaceutical dosage form of the present invention, containing nifedipine, and counsels the patient on the necessity to take the pharmaceutical dosage form of the present invention in an intact form.

Example 3

Patient C was recently prescribed a pharmaceutical composition of the present invention, which contains 20 mg of an antianxiety medication. Patient C has previously been prescribed 10 mg of the same medication, in the following dosage forms: (1) an intact 10 mg tablet pharmaceutical dosage form of the present invention, (2) an intact 10 mg tablet dosage form that is not a composition of the present invention; and (3) a 20 mg tablet dosage form that is not a composition of the present invention, which she divided into two pieces. Patient C splits a 20 mg tablet dosage form that she was recently prescribed, which is a composition of the present invention, into two pieces.

Patient C begins to experience an anxiety attack and takes one of the divided pieces. In the past, administration of 10 mg of the drug, taken in one of the three ways described above, provided Patient C will full relief of her anxiety symptoms within 30 minutes. Only at about one hour after administration of the divided piece, Patient C begins to feel some relief. However, even after two hours after administration, Patient C still does not experience the full relief of anxiety symptoms she usually experiences after administration of 10 mg of the drug, taken in one of the three ways described above. Patient C realizes that dividing the 20 mg dosage form of the present invention provides her with ineffective therapeutic benefit.

What is claimed:

1. An oral pharmaceutical composition comprising a monolithic dosage form,
wherein the dosage form comprises an inner expansion layer comprising an expansion polymer; a barrier layer substantially covering the expansion layer and comprising a barrier polymer selected from the group consisting of: polyacrylates or copolymers thereof, and mixtures thereof; and a diffusion layer substantially covering the barrier layer and comprising a drug and a diffusion polymer selected from the group consisting of: quarternary ammonium acrylic or methacrylic polymers, acrylic or methacrylic polymers, acrylic or methacrylic copolymers, and mixtures thereof, wherein the barrier layer is bonded to the diffusion layer, and the barrier layer and diffusion layer are cured, and wherein the drug is substantially homogeneously distributed within the diffusion polymer and diffuses from the diffusion layer within the gastrointestinal tract, wherein the diffusion layer has a thickness of about 0.1 to 1.0 mm, and
wherein the dosage form is divided into more than one piece, the bond between the diffusion layer and barrier layer is substantially preserved, and
wherein when the dosage form is divided into more than one piece and at least one of the pieces is administered to a subject, the Cmax and/or AUC achieved at 4 hours after administration is substantially the same or lower than the Cmax and/or AUC achieved at 4 hours after administration of a comparable composition in an intact dosage form of equal drug dosage of the administered at least one piece,
and wherein the drug is an opioid.

2. The pharmaceutical composition of claim 1, wherein the Cmax and/or AUC achieved after 8 hours after administration is at least about 20% lower than the Cmax and/or AUC achieved at 4 hours after administration of a comparable composition in an intact dosage form of equal drug dosage of the administered at least one piece.

3. An oral pharmaceutical composition comprising a monolithic dosage form,
wherein the dosage form comprises an inner expansion layer comprising an expansion polymer; a barrier layer substantially covering the expansion layer and comprising a barrier polymer selected from the group consisting of: polyacrylates or copolymers thereof and mixtures thereof; and a diffusion layer substantially covering the barrier layer and comprising a drug and a diffusion polymer selected from the group consisting of: quarternary ammonium acrylic or methacrylic polymers, acrylic or methacrylic polymers, acrylic or methacrylic copolymers, and mixtures thereof, wherein the barrier layer is bonded to the diffusion layer, and the barrier layer and diffusion layer are cured, and wherein the drug is substantially homogeneously distributed within the diffusion polymer and diffuses from the diffusion layer within the gastrointestinal tract, wherein the diffusion layer has a thickness of about 0.1 to 1.0 mm, and wherein the dosage form is divided into more than one piece, the bond between the diffusion layer and barrier layer is substantially preserved, and wherein when the dosage form is divided into more than one piece and at least one of the pieces is administered to a subject, the rate of drug released from the dosage form at 4 hours after administration is substantially the same as the rate of drug released at 4 hours after administration from a comparable composition in an intact dosage form of equal drug dosage of the administered at least one piece, and wherein the drug is an opioid.

4. An oral pharmaceutical composition comprising a monolithic dosage form, wherein the dosage form comprises an inner expansion layer comprising an expansion polymer; a barrier layer substantially covering the expansion layer and comprising a barrier polymer selected from the group consisting of: polyacrylates or copolymers thereof and mixtures thereof; and a diffusion layer substantially covering the barrier layer and comprising a drug and a diffusion polymer selected from the group consisting of: quarternary ammonium acrylic or methacrylic polymers, acrylic or methacrylic polymers, acrylic or methacrylic copolymers and mixtures thereof, wherein the barrier layer is bonded to the diffusion layer, and the barrier layer and diffusion layer are cured, and wherein the drug is substantially homogeneously distributed within the diffusion polymer and diffuses from the diffusion layer within the gastrointestinal tract, wherein the diffusion layer has a thickness of about 0.1 to 1.0 mm, and wherein the dosage form is divided into more than one piece, the bond between the diffusion layer and barrier layer is substantially preserved, and wherein when the dosage form is divided into more than one piece and at least one of the pieces is administered to a subject, the Tmax achieved after administration is substantially the same or greater than the Tmax achieved after administration of a comparable composition in an intact dosage form of equal drug dosage of the administered at least one piece, and the drug is an opioid.

5. The pharmaceutical composition of claim 4, wherein the Tmax achieved after administration is at least about 20% greater than the Tmax achieved after administration of comparable composition in an intact dosage form of equal drug dosage of the administered at least one piece.

6. An oral pharmaceutical composition comprising a monolithic dosage form, wherein the dosage form comprises an inner expansion layer comprising an expansion polymer; a barrier layer substantially covering the expansion layer and comprising a barrier polymer selected from the group consisting of: polyacrylates or copolymers thereof and mixtures thereof; and a diffusion layer substantially covering the barrier layer and comprising a drug and a diffusion polymer selected from the group consisting of: quarternary ammonium acrylic or methacrylic polymers, acrylic or methacrylic polymers, acrylic or methacrylic copolymers and mixtures thereof, wherein the barrier layer is bonded to the diffusion layer, and the barrier layer and diffusion layer are cured, and wherein the drug is substantially homogeneously distributed within the diffusion polymer and diffuses from the diffusion layer within the gastrointestinal tract, wherein the diffusion layer has a thickness of about 0.1 to 1.0 mm, and wherein the dosage form is divided into more than one piece, the bond between the diffusion layer and barrier layer is substantially preserved, and wherein when the dosage form is divided into more than one piece and at least one of the pieces is administered to a subject, the Cmax and/or AUC achieved at 4 hours after administration is substantially the same or lower than the Cmax and/or AUC achieved at 4 hours after administration of an intact dosage form of a bioequivalent drug composition, wherein the drug dosage in the intact dosage form of the bioequivalent drug composition is equal to the drug dosage of the administered at least one piece, and wherein the drug is an opioid.

7. The pharmaceutical composition of claim 6, wherein the Cmax and/or AUC achieved at 4 hours after administration, is at least about 20% lower than the Cmax and/or AUC achieved after administration of the intact dosage form of the bioequivalent drug composition.

8. An oral pharmaceutical composition comprising a monolithic dosage form, wherein the dosage form comprises an inner expansion layer comprising an expansion polymer; a barrier layer substantially covering the expansion layer and comprising a barrier polymer selected from the group consisting of: polyacrylates or copolymers thereof and mixtures thereof; and a diffusion layer substantially covering the barrier layer and comprising a drug and a diffusion polymer selected from the group consisting of; quarternary ammonium acrylic or methacrylic polymers, acrylic or methacrylic polymers, acrylic or methacrylic copolymers and mixtures thereof, wherein the barrier layer is bonded to the diffusion layer, and the barrier layer and diffusion layer are cured, and wherein the drug is substantially homogeneously distributed within the diffusion polymer and diffuses from the diffusion layer within the gastrointestinal tract, wherein the diffusion layer has a thickness of about 0.1 to 1.0 mm, and wherein the dosage form is divided into more than one piece, the bond between the diffusion layer and barrier layer is substantially preserved, and wherein when the dosage form is divided into more than one piece and at least one of the pieces is administered to a subject, the rate of drug released from the dosage form at 4 hours after administration is substantially the same or lower than the rate of drug released from an intact dosage form of a bioequivalent drug composition at 4 hours after administration, wherein the drug dosage in the intact dosage form of the bioequivalent drug composition is equal to the drug dosage of the administered at least one piece, and wherein the drug is an opioid.

9. The pharmaceutical composition of claim 8, wherein the rate of drug released from the composition at 4 hours after administration is at least about 20% lower than the rate of drug released from the intact dosage form of the bioequivalent drug composition.

10. An oral pharmaceutical composition comprising a monolithic dosage form, wherein the dosage form comprises an inner expansion layer comprising an expansion polymer; a barrier layer substantially covering the expansion layer and comprising a barrier polymer selected from the group consisting of: polyacrylates or copolymers thereof and mixtures thereof; and a diffusion layer substantially covering the barrier layer and comprising a drug and a diffusion polymer selected from the group consisting of: quarternary ammonium acrylic or methacrylic polymers, acrylic or methacrylic polymers, acrylic or methacrylic copolymers and mixtures thereof, wherein the barrier layer is bonded to the diffusion layer, and the barrier layer and diffusion layer are cured, and wherein the drug is substantially homogeneously distributed within the diffusion polymer and diffuses from the diffusion layer within the gastrointestinal tract, wherein the diffusion layer has a thickness of about 0.1 to 1.0 mm, and wherein the dosage form is divided into more than one piece, the bond between the diffusion layer and barrier layer is substantially preserved, and wherein when the dosage form is divided into more than one piece and at least one of the pieces is administered to a subject, the Tmax achieved after administration is substantially the same or greater than the Tmax achieved administration of an intact dosage form of a bioequivalent drug composition, wherein the drug dosage in the intact dosage form of the bioequivalent drug composition is equal to the drug dosage of the administered at least one piece, and wherein the drug is an opioid.

11. The pharmaceutical composition of claim 10, wherein the Tmax achieved after administration is at least about 20% greater than the Tmax achieved after administration of the intact dosage form of the bioequivalent drug composition.

12. An oral pharmaceutical composition comprising a monolithic dosage form, wherein the dosage form comprises an inner expansion layer comprising an expansion polymer; a barrier layer substantially covering the expansion layer and comprising a barrier polymer selected from the group consisting of: polyacrylates or copolymers thereof and mixtures thereof; and a diffusion layer substantially covering the barrier layer and comprising a drug and a diffusion polymer selected from the group consisting of: qua ternary ammonium acrylic or methacrylic polymers, acrylic or methacrylic polymers, acrylic or methacrylic copolymers and mixtures thereof, wherein the barrier layer is bonded to the diffusion layer, and the barrier layer and diffusion layer are cured, and wherein the drug is substantially homogeneously distributed within the diffusion polymer and diffuses from the diffusion layer within the gastrointestinal tract, wherein the diffusion layer has a thickness of about 0.1 to 1.0 mm, and wherein the dosage form is divided into more than one piece, the bond between the diffusion layer and barrier layer is substantially preserved, and wherein when the dosage form is divided into more than one piece and at least one of the pieces is administered to a subject, the Cmax and/or AUC achieved at 4 hours after administration is substantially the same or lower than the Cmax and/or AUC achieved at 4 hours after administration of a divided piece of a bioequivalent drug composition, wherein the divided piece of the bioequivalent drug composition comprises a drug dosage equal to the drug dosage of the administered at least one piece, and wherein the drug is an opioid.

13. The pharmaceutical composition of claim 12, wherein the Cmax and/or AUC achieved at 4 hours after administration, is at least about 20% lower than the Cmax and/or AUC achieved at 4 hours after administration of a divided piece of a bioequivalent drug composition, wherein the divided piece of the bioequivalent drug composition comprises a drug dosage equal to the drug dosage of the administered at least one piece.

14. An oral pharmaceutical composition comprising a monolithic dosage form, wherein the dosage form comprises an inner expansion layer comprising an expansion polymer; a barrier layer substantially covering the expansion layer and comprising a barrier polymer selected from the group consisting of: polyacrylates or copolymers thereof and mixtures thereof; and a diffusion layer substantially covering the barrier layer and comprising a drug and a diffusion polymer selected from the group consisting of; quarternary ammonium acrylic or methacrylic polymers, acrylic or methacrylic polymers, acrylic or methacrylic copolymers and mixtures thereof, wherein the barrier layer is bonded to the diffusion layer, and the barrier layer and diffusion layer are cured, and wherein the drug is substantially homogeneously distributed within the diffusion polymer and diffuses from the diffusion layer within the gastrointestinal tract, wherein the diffusion layer has a thickness of about 0.1 to 1.0 mm, and wherein the dosage form is divided into more than one piece, the bond between the diffusion layer and barrier layer is substantially preserved, and wherein when the dosage form is divided into more than one piece and at least one of the pieces is administered to a subject, the rate of drug released from the dosage form at 4 hours after administration is substantially the same or lower than the rate of drug released at 4 hours after administration from a divided piece of a bioequivalent drug composition, wherein the divided piece of the bioequivalent drug composition comprises a drug dosage equal to the drug dosage of the administered at least one piece, and wherein the drug is an opioid.

15. The pharmaceutical composition of claim 14, wherein the rate of drug released from the composition at 4 hours after administration is at least about 20% lower than the rate of drug released at 4 hours after administration from a divided piece of a bioequivalent drug composition, wherein the divided piece of the bioequivalent drug composition comprises a drug dosage equal to the drug dosage of the administered at least one piece.

16. An oral pharmaceutical composition comprising a monolithic dosage form, wherein the dosage form comprises an inner expansion layer comprising an expansion polymer; a barrier layer substantially covering the expansion layer and comprising a barrier polymer selected from the group consisting of: polyacrylates or copolymers thereof and mixtures thereof; and a diffusion layer substantially covering the barrier layer and comprising a drug and a diffusion polymer selected from the group consisting of: quarternary ammonium acrylic or methacrylic polymers, acrylic or methacrylic polymers, acrylic or methacrylic copolymers and mixtures thereof, wherein the barrier layer is bonded to the diffusion layer, and the barrier layer and diffusion layer are cured, and wherein the drug is substantially homogeneously distributed within the diffusion polymer and diffuses from the diffusion layer within the gastrointestinal tract, wherein the diffusion layer has a thickness of about 0.1 to 1.0 mm, and wherein the dosage form is divided into more than one piece, the bond between the diffusion layer and barrier layer is substantially preserved, and wherein when the dosage form is divided into more than one piece and at least one of the pieces is administered to a subject, the Tmax achieved after administration is substantially the same or greater than the Tmax achieved after administration of a divided piece of a bioequivalent drug composition, wherein the divided piece of the bioequivalent drug composition comprises a drug dosage equal to the drug dosage of the administered at least one piece, and wherein the drug is an opioid.

17. The pharmaceutical composition of claim 16, wherein the Tmax achieved after administration is at least about 20% greater than the Tmax achieved after administration of a divided piece of a bioequivalent drug composition, wherein the divided piece of the bioequivalent drug composition comprises a drug dosage equal to the drug dosage of the administered at least one piece.

18. An oral pharmaceutical composition comprising a monolithic dosage form, wherein the dosage form comprises an inner expansion layer comprising an expansion polymer; a barrier layer substantially covering the expansion layer and comprising a barrier polymer selected from the group consisting of: polyacrylates or copolymers thereof and mixtures thereof; and a diffusion layer substantially covering the barrier layer and comprising a drug and a diffusion polymer selected from the group consisting of: quarternary ammonium acrylic or methacrylic polymers, acrylic or methacrylic polymers, acrylic or methacrylic copolymers, and mixtures thereof, wherein the barrier layer is bonded to the diffusion layer, and the barrier layer and diffusion layer are cured, and wherein the drug is substantially homogeneously distributed within the diffusion polymer and diffuses from the diffusion layer within the gastrointestinal tract, wherein the diffusion layer has a thickness of about 0.1 to 1.0 mm, and wherein the dosage form is divided into more than one piece, the bond between the diffusion layer and barrier layer is substantially preserved, and wherein when the dosage form is divided into more than one piece and at least one of the pieces is administered to a subject, the rate of drug released from the dosage form at 4 hours after administration is at least about 10% lower than the rate of drug released at 4 hours after administration from a comparable composition in an intact dosage form of equal drug dosage of the administered at least one piece, and wherein the drug is an opioid.

19. The pharmaceutical composition of claim 18, wherein the rate of drug released from the composition at 4 hours after administration is at least about 20% lower than the rate of drug released at 4 hours after administration from a comparable composition in an intact dosage form of equal drug dosage of the administered at least one piece.

20. An oral pharmaceutical composition comprising a monolithic dosage form, wherein the dosage form comprises an inner expansion layer comprising an expansion polymer; a barrier layer substantially covering the expansion layer and comprising a barrier polymer selected from the group consisting of: polyacrylates or copolymers thereof and mixtures thereof; and a diffusion layer substantially covering the barrier layer and comprising a drug and a diffusion polymer selected from the group consisting of: quarternary ammonium acrylic or methacrylic polymers, acrylic or methacrylic polymers, acrylic or methacrylic copolymers, and mixtures thereof, wherein the barrier layer is bonded to the diffusion layer, and the barrier layer and diffusion layer are cured, and wherein the drug is substantially homogeneously distributed within the diffusion polymer and diffuses from the diffusion layer within the gastrointestinal tract, wherein the diffusion layer comprises about 1 to 30% of the total thickness of the composition, and wherein the dosage form is divided into more than one piece, the bond between the diffusion layer and barrier layer is substantially preserved, and wherein when the dosage form is divided into more than one piece and at least one of the pieces is administered to a subject, the Cmax and/or AUC achieved at 4 hours after administration is substantially the same or lower than the Cmax and/or AUC achieved at 4 hours after administration of a comparable composition in an intact dosage form of equal drug dosage of the administered at least one piece, and wherein the drug is an opioid.

21. The pharmaceutical composition of claim 20, wherein the Cmax and/or AUC achieved at 4 hours after administration is at least about 20%® lower than the Cmax and/or AUC achieved at 4 hours after administration of a comparable composition in an intact dosage form of equal drug dosage of the administered at least one piece.

22. An oral pharmaceutical composition comprising a monolithic dosage form, wherein the dosage form comprises an inner expansion layer comprising an expansion polymer; a barrier layer substantially covering the expansion layer and comprising a barrier polymer selected from the group consisting of: polyacrylates or copolymers thereof, and mixtures thereof; and a diffusion layer substantially covering the barrier layer and comprising a drug, and a diffusion polymer selected from the group consisting of: quarternary ammonium acrylic or methacrylic polymers, acrylic or methacrylic polymers, acrylic or methacrylic copolymers, and mixtures thereof, wherein the barrier layer is bonded to the diffusion layer, and the barrier layer and diffusion layer are cured, and wherein the drug is substantially homogeneously distributed within the diffusion polymer and diffuses from the diffusion layer within the gastrointestinal tract, wherein the diffusion layer comprises about 1 to 30% of the total thickness of the composition, and wherein the dosage form is divided into more than one piece, the bond between the diffusion layer and barrier layer is substantially preserved, and when the dosage form is divided into more than one piece and at least one of the pieces is administered to a subject, the rate of drug released from the dosage form at 4 hours after administration is substantially the same as the rate of drug released at 4 hours after administration from a comparable composition in an intact dosage form of equal drug dosage of the administered at least one piece, and wherein the drug is an opioid.

23. An oral pharmaceutical composition comprising a monolithic dosage form,
wherein the dosage form comprises an inner expansion layer comprising an expansion polymer; a barrier layer substantially covering the expansion layer and comprising a barrier polymer selected from the group consisting of: polyacrylates or copolymers thereof, and mixtures thereof; and a diffusion layer substantially covering the barrier layer and comprising a drug and a diffusion polymer selected from the group consisting of: quarternary ammonium acrylic or methacrylic polymers, acrylic or methacrylic, polymers, acrylic or methacrylic copolymers, and mixtures thereof, wherein the barrier layer is bonded to the diffusion layer, and the barrier layer and diffusion layer are cured, and wherein the drug is substantially homogeneously distributed within the diffusion polymer and diffuses from the diffusion layer within the gastrointestinal tract, wherein the diffusion layer comprises about 1 to 30% of the total thickness of the composition, and
wherein the dosage form is divided into more than one piece, the bond between the diffusion layer and barrier layer is substantially preserved, and
wherein when the dosage form is divided into more than one piece and at least one of the pieces is administered to a subject, the Tmax achieved after administration is substantially the same or greater than the Tmax achieved after administration of a comparable composition in an intact dosage form of equal drug dosage of the administered at least one piece,
and the drug is an opioid.

24. The pharmaceutical composition of claim 23, wherein the Tmax achieved after administration is at least about 20% greater than the Tmax achieved after administration of comparable composition in an intact dosage form of equal drug dosage of the administered at least one piece.

25. An oral pharmaceutical composition comprising a monolithic dosage form,
wherein the dosage form comprises an inner expansion layer comprising an expansion polymer; a barrier layer substantially covering the expansion layer and comprising a barrier polymer selected from the group consisting of: polyacrylates or copolymers thereof and mixtures thereof; and a diffusion layer substantially covering the barrier layer and comprising a drug and a diffusion polymer selected from the group consisting of: quarternary ammonium acrylic or methacrylic polymers, acrylic or methacrylic polymers, acrylic or methacrylic copolymers, and mixtures thereof, wherein the barrier layer is bonded to the diffusion layer, and the barrier layer and diffusion layer are cured, and wherein the drug is substantially homogeneously distributed within the diffusion polymer and diffuses from the diffusion layer within the gastrointestinal tract, wherein the diffusion layer comprises about 1 to 30% of the total thickness of the composition, and
wherein the dosage form is divided into more than one piece, the bond between the diffusion layer and barrier layer is substantially preserved, and
wherein when the dosage form is divided into more than one piece and at least one of the pieces is administered to a subject, the Cmax and/or AUC achieved at 4 hours after administration is substantially the same or lower than the Cmax and/or AUC achieved at 4 hours after administration of an intact dosage form of a bioequivalent drug composition, wherein the drug dosage in the intact dosage form of the bioequivalent drug composition is equal to the drug dosage of the administered at least one piece,
and wherein the drug is an opioid.

26. The pharmaceutical composition of claim 25, wherein the Cmax and/or AUC achieved at 4 hours after administration is at least about 20% lower than the Cmax and/or AUC achieved at 4 hours after administration of the intact dosage form of the bioequivalent drug composition.

27. An oral pharmaceutical composition comprising a monolithic dosage form,
wherein the dosage form comprises an inner expansion layer comprising an expansion polymer; a barrier layer substantially covering the expansion layer and comprising a barrier polymer selected from the group consisting of: polyacrylates or copolymers thereof, and mixtures thereof; and a diffusion layer substantially covering the barrier layer and comprising a drug and a diffusion polymer selected from the group consisting of: quarternary ammonium acrylic or methacrylic polymers, acrylic or methacrylic polymers, acrylic or methacrylic copolymers, and mixtures thereof, wherein the barrier layer is bonded to the diffusion layer, and the barrier layer and diffusion layer are cured, and wherein the drug is substantially homogeneously distributed within the diffusion polymer and diffuses from the diffusion layer within the gastrointestinal tract, wherein the diffusion layer comprises about 1 to 30% of the total thickness of the composition, and
wherein the dosage form is divided into more than one piece, the bond between the diffusion layer and barrier layer is substantially preserved, and
wherein when the dosage form is divided into more than one piece and at least one of the pieces is administered to a subject, the rate of drug released from the dosage form at 4 hours after administration is substantially the same or lower than the rate of drug released at 4 hours after administration from an intact dosage form of a bioequivalent drug composition, wherein the drug dosage in the intact dosage form of the bioequivalent drug composition is equal to the drug dosage of the administered at least one piece,
and wherein the drug is an opioid.

28. The pharmaceutical composition of claim 27, wherein the rate of drug released from the composition at 4 hours after administration is at least about 20% lower than the rate of drug released at 4 hours after administration from the intact dosage form of the bioequivalent drug composition.

29. An oral pharmaceutical composition comprising a monolithic dosage form,
wherein the dosage form comprises an inner expansion layer comprising an expansion polymer; a barrier layer substantially covering the expansion layer and comprising a barrier polymer selected from the group consisting of: polyacrylates or copolymers thereof and mixtures thereof; and a diffusion layer substantially covering the barrier layer and comprising a drug and a diffusion polymer selected from the group consisting of: quarternary ammonium acrylic or methacrylic polymers, acrylic or methacrylic polymers, acrylic or methacrylic copolymers, and mixtures thereof, wherein the barrier layer is bonded to the diffusion layer, and the barrier layer and diffusion layer are cured, and wherein the drug is substantially homogeneously distributed within the diffusion polymer and diffuses from the diffusion layer within the gastrointestinal tract, wherein the diffusion layer comprises about 1 to 30% of the total thickness of the composition, and wherein the dosage form is divided into more than one piece, the bond between the diffusion layer and barrier layer is substantially preserved, and wherein when the dosage form is divided into more than one piece and at least one of the pieces is administered to a subject, the Tmax achieved after administration is substantially the same or greater than the Tmax achieved administration of an intact dosage form of a bioequivalent drug composition, wherein the drug dosage in the intact dosage form of the bioequivalent drug composition is equal to the drug dosage of the administered at least one piece, and wherein the drug is an opioid.

30. The pharmaceutical composition of claim 29, wherein the Tmax achieved after administration is at least about 20% greater than the Tmax achieved after administration of the intact dosage form, of the bioequivalent drug composition.

31. An oral pharmaceutical composition comprising a monolithic dosage form, wherein the dosage form comprises an inner expansion layer comprising an expansion polymer; a barrier layer substantially covering the expansion layer and comprising a barrier polymer selected from the group consisting of; polyacrylates or copolymers thereof and mixtures thereof; and a diffusion layer substantially covering the barrier layer and comprising a drug and a diffusion polymer selected from the group consisting of: quarternary ammonium acrylic or methacrylic polymers, acrylic or methacrylic polymers, acrylic or methacrylic copolymers, and mixtures thereof, wherein the barrier layer is bonded to the diffusion layer, and the barrier layer and diffusion layer are cured, and wherein the drug, is substantially homogeneously distributed within the diffusion polymer and diffuses from the diffusion layer within the gastrointestinal tract, wherein the diffusion layer comprises about 1 to 30% of the total thickness of the composition, and wherein the dosage form is divided into more than one piece, the bond between the diffusion layer and barrier layer is substantially preserved, and wherein when the dosage form is divided into more than one piece and at least one of the pieces is administered to a subject, the Cmax and/or AUC achieved at 4 hours after administration is substantially the same or lower than the Cmax and/or AUC achieved at 4 hours after administration of a divided piece of a bioequivalent drug composition, wherein the divided piece of the bioequivalent drug composition comprises a drug, dosage equal to the drug dosage of the administered at least one piece, and wherein the drug is an opioid.

32. The pharmaceutical composition of claim 31, wherein the Cmax and/or AUC achieved at 4 hours after administration is at least about 20% lower than the Cmax and/or AUC achieved at 4 hours after administration of a divided piece of a bioequivalent drug composition, wherein the divided piece of the bioequivalent drug composition comprises a drug dosage equal to the drug dosage of the administered at least one piece.

33. An oral pharmaceutical composition comprising a monolithic dosage form, wherein the dosage form comprises an inner expansion layer comprising an expansion polymer; a barrier layer substantially covering the expansion layer and comprising a barrier polymer selected from the group consisting of: polyacrylates or copolymers thereof and mixtures thereof; and a diffusion layer substantially covering the barrier layer and comprising a drug and a diffusion polymer selected from the group consisting of: quarternary ammonium acrylic or methacrylic polymers, acrylic or methacrylic polymers, acrylic or methacrylic copolymers, and mixtures thereof, wherein the barrier layer is bonded to the diffusion layer, and the barrier layer and diffusion layer are cured, and wherein the drug is substantially homogeneously distributed within the diffusion polymer and diffuses from the diffusion layer within the gastrointestinal tract, wherein the diffusion layer comprises about 1 to 30% of the total thickness of the composition, and wherein the dosage form is divided into more than one piece, the bond between the diffusion layer and barrier layer is substantially preserved, and wherein when the dosage form is divided into more than one piece and at least one of the pieces is administered to a subject, the rate of drug released from the dosage form at 4 hours after administration is substantially the same or lower than the rate of drug released at 4 hours after administration from a divided piece of a bioequivalent drug composition, wherein the divided piece of the bioequivalent drug composition comprises a drug dosage equal to the drug dosage of the administered at least one piece and wherein the drug is an opioid.

34. The pharmaceutical composition of claim 33, wherein the rate of drug released from the composition at 4 hours after administration is at least about 20% lower than the rate of drug released at 4 hours after administration from a divided piece of a bioequivalent drug composition, wherein the divided piece of the bioequivalent drug composition comprises a drug dosage equal to the drug dosage of the administered at least one piece.

35. An oral pharmaceutical composition comprising a monolithic dosage form, wherein the dosage form comprises an inner expansion layer comprising an expansion polymer; a barrier layer substantially covering the expansion layer and comprising a barrier polymer selected from the group consisting of: polyacrylates or copolymers thereof and mixtures thereof; and a diffusion layer substantially covering the barrier layer and comprising a drug and a diffusion polymer selected from the group consisting of: quarternary ammonium acrylic or methacrylic polymers, acrylic or methacrylic polymers, acrylic or methacrylic copolymers, and mixtures thereof, wherein the barrier layer is bonded to the diffusion layer, and the barrier layer and diffusion layer are cured, and wherein the drug is substantially homogeneously distributed within the diffusion polymer and diffuses from the diffusion layer within the gastrointestinal tract, wherein the diffusion layer comprises about 1 to 30% of the total thickness of the composition, and wherein the dosage form is divided into more than one piece, the bond between the diffusion layer and barrier layer is substantially preserved, and wherein when the dosage form is divided into more than one piece and at least one of the pieces is administered to a subject, the Tmax achieved after administration is substantially the same or greater than the Tmax achieved after administration of a divided piece of a bioequivalent drug composition, wherein the divided piece of the bioequivalent drug composition comprises a drug dosage equal to the drug dosage of the administered at least one piece,
and wherein the drug is an opioid.

36. The pharmaceutical composition of claim 35, wherein the Tmax achieved after administration is at least about 20% greater than the Tmax achieved after administration of a divided piece of a bioequivalent drug composition, wherein the divided piece of the bioequivalent drug composition comprises a drug dosage equal to the drug dosage of the administered at least one piece.

37. An oral pharmaceutical composition comprising a monolithic dosage form,
wherein the dosage form comprises an inner expansion layer comprising an expansion polymer; a barrier layer substantially covering the expansion layer and comprising a barrier polymer selected from the group consisting of: polyacrylates or copolymers thereof and mixtures thereof; and, a diffusion layer substantially covering the barrier layer and comprising a drug and a diffusion polymer selected from the group consisting of: quarternary ammonium acrylic or methacrylic polymers, acrylic or methacrylic polymers, acrylic or methacrylic copolymers, and mixtures thereof, wherein the barrier layer is bonded to the diffusion layer, and the barrier layer and diffusion layer are cured, and wherein the drug is substantially homogeneously distributed within the diffusion polymer and diffuses from the diffusion layer within the gastrointestinal tract, wherein the diffusion layer comprises about 1 to 30% of the total thickness of the composition, and
wherein the dosage form is divided into more than one piece, the bond between the diffusion layer and barrier layer is substantially preserved, and
wherein when the dosage form is divided into more than one piece and at least one of the pieces is administered to a subject, the rate of drug released from the dosage form at 4 hours after administration is at least about 10% lower than the rate of drug released at 4 hours after administration from a comparable composition in an intact dosage form of equal drug dosage of the administered at least one piece,
and wherein the drug is an opioid.

38. The pharmaceutical composition of claim 37, wherein the rate of drug released from the composition at 4 hours after administration is at least about 20% lower than the rate of drug released at 4 hours after administration from a comparable composition in an intact dosage form of equal drug dosage of the administered at least one piece.

39. The pharmaceutical composition of claim 1, wherein the drug is hydrocodone.

40. The pharmaceutical composition of claim 1, wherein the drug is morphine.

41. The pharmaceutical composition of claim 1, wherein the drug is oxycodone.

42. The pharmaceutical composition of claim 1, wherein the drug is hydromorphone.

43. The pharmaceutical composition of claim 1, wherein the drug is oxymorphone.

44. The pharmaceutical composition of claim 3, wherein the drug is hydrocodone.

45. The pharmaceutical composition of claim 3, wherein the drug is morphine.

46. The pharmaceutical composition of claim 3, wherein the drug is oxycodone.

47. The pharmaceutical composition of claim 3, wherein the drug is hydromorphone.

48. The pharmaceutical composition of claim 3, wherein the drug is oxymorphone.

49. The pharmaceutical composition of claim 4, wherein the drug is hydrocodone.

50. The pharmaceutical composition of claim 4, wherein the drug is morphine.

51. The pharmaceutical composition of claim 4, wherein the drug is oxycodone.

52. The pharmaceutical composition of claim 4, wherein the drug is hydromorphone.

53. The pharmaceutical composition of claim 4, wherein the drug is oxymorphone.

54. The pharmaceutical composition of claim 6, wherein the drug is hydrocodone.

55. The pharmaceutical composition of claim 6, wherein the drug is morphine.

56. The pharmaceutical composition of claim 6, wherein the drug is oxycodone.

57. The pharmaceutical composition of claim 6, wherein the drug is hydromorphone.

58. The pharmaceutical composition of claim 6, wherein the drug is oxymorphone.

59. The pharmaceutical composition of claim 8, wherein the drug is hydrocodone.

60. The pharmaceutical composition of claim 8, wherein the drug is morphine.

61. The pharmaceutical composition of claim 8, wherein the drug is oxycodone.

62. The pharmaceutical composition of claim 8, wherein the drug is hydromorphone.

63. The pharmaceutical composition of claim 8, wherein the drug is oxymorphone.

64. The pharmaceutical composition of claim 10, wherein the drug is hydrocodone.

65. The pharmaceutical composition of claim 10, wherein the drug is morphine.

66. The pharmaceutical composition of claim 10, wherein the drug is oxycodone.

67. The pharmaceutical composition of claim 10, wherein the drug is hydromorphone.

68. The pharmaceutical composition of claim 10, wherein the drug is oxymorphone.

69. The pharmaceutical composition of claim 12, wherein the drug is hydrocodone.

70. The pharmaceutical composition of claim 12, wherein the drug is morphine.

71. The pharmaceutical composition of claim 12, wherein the drug is oxycodone.

72. The pharmaceutical composition of claim 12, wherein the drug is hydromorphone.

73. The pharmaceutical composition of claim 12, wherein the drug is oxymorphone.

74. The pharmaceutical composition of claim 14, wherein the drug is hydrocodone.

75. The pharmaceutical composition of claim 14, wherein the drug is morphine.

76. The pharmaceutical composition of claim 14, wherein the drug is oxycodone.

77. The pharmaceutical composition of claim 14, wherein the drug is hydromorphone.

78. The pharmaceutical composition of claim 14, wherein the drug is oxymorphone.

79. The pharmaceutical composition of claim 16, wherein the drug is hydrocodone.

80. The pharmaceutical composition of claim 16, wherein he drug is morphine.

81. The pharmaceutical composition of claim 16, wherein the drug is oxycodone.

82. The pharmaceutical composition of claim 16, wherein the drug is hydromorphone.

83. The pharmaceutical composition of claim 16, wherein the drug is oxymorphone.

84. The pharmaceutical composition of claim 18, wherein the drug is hydrocodone.

85. The pharmaceutical composition of claim 18, wherein the drug is morphine.

86. The pharmaceutical composition of claim 18, wherein the drug is oxycodone.

87. The pharmaceutical composition of claim 18, wherein the drug is hydromorphone.

88. The pharmaceutical composition of claim 18, wherein the drug is oxymorphone.

89. The pharmaceutical composition of claim 20, wherein the drug is hydrocodone.

90. The pharmaceutical composition of claim 20, wherein the drug is morphine.

91. The pharmaceutical composition of claim 20, wherein the drug is oxycodone.

92. The pharmaceutical composition of claim 20, wherein the drug is hydromorphone.

93. The pharmaceutical composition of claim 20, wherein the drug is oxymorphone.

94. The pharmaceutical composition of claim 22, wherein the drug is hydrocodone.

95. The pharmaceutical composition of claim 22, wherein the drug is morphine.

96. The pharmaceutical composition of claim 22, wherein the drug is oxycodone.

97. The pharmaceutical composition of claim 22, wherein the drug is hydromorphone.

98. The pharmaceutical composition of claim 22, wherein the drug is oxymorphone.

99. The pharmaceutical composition of claim 23, wherein the drug is hydrocodone.

100. The pharmaceutical composition of claim 23, wherein the drug is morphine.

101. The pharmaceutical composition of claim 23, wherein the drug is oxycodone.

102. The pharmaceutical composition of claim 23, wherein the drug is hydromorphone.

103. The pharmaceutical composition of claim 23, wherein the drug is oxymorphone.

104. The pharmaceutical composition of claim 25, wherein the drug is hydrocodone.

105. The pharmaceutical composition of claim 25, wherein the drug is morphine.

106. The pharmaceutical composition of claim 25, wherein the drug is oxycodone.

107. The pharmaceutical composition of claim 25, wherein the drug is hydromorphone.

108. The pharmaceutical composition of claim 25, wherein the drug is oxymorphone.

109. The pharmaceutical composition of claim 27, wherein the drug is hydrocodone.

110. The pharmaceutical composition of claim 27, wherein the drug is morphine.

111. The pharmaceutical composition of claim 27, wherein the drug is oxycodone.

112. The pharmaceutical composition of claim 27, wherein the drug is hydromorphone.

113. The pharmaceutical composition of claim 27, wherein the drug is oxymorphone.

114. The pharmaceutical composition of claim 29, wherein the drug is hydrocodone.

115. The pharmaceutical composition of claim 29, wherein the drug is morphine.

116. The pharmaceutical composition of claim 29, wherein the drug is oxycodone.

117. The pharmaceutical composition of claim 29, wherein the drug is hydromorphone.

118. The pharmaceutical composition of claim 29, wherein the drug is oxymorphone.

119. The pharmaceutical composition of claim 31, wherein the drug is hydrocodone.

120. The pharmaceutical composition of claim 31, wherein the drug is morphine.

121. The pharmaceutical composition of claim 31, wherein the drug is oxycodone.

122. The pharmaceutical composition of claim 31, wherein the drug is hydromorphone.

123. The pharmaceutical composition of claim 31, wherein the drug is oxymorphone.

124. The pharmaceutical composition of claim 33, wherein the drug is hydrocodone.

125. The pharmaceutical composition of claim 33, wherein the drug is morphine.

126. The pharmaceutical composition of claim 33, wherein the drug is oxycodone.

127. The pharmaceutical composition of claim 33, wherein the drug is hydromorphone.

128. The pharmaceutical composition of claim 33, wherein the drug is oxymorphone.

129. The pharmaceutical composition of claim 35, wherein the drug is hydrocodone.

130. The pharmaceutical composition of claim 35, wherein the drug is morphine.

131. The pharmaceutical composition of claim 35, wherein the drug is oxycodone.

132. The pharmaceutical composition of claim 35, wherein the drug is hydromorphone.

133. The pharmaceutical composition of claim 35, wherein the drug is oxymorphone.

134. The pharmaceutical composition of claim 37, wherein the hydrocodone.

135. The pharmaceutical composition of claim 37, wherein the drug is morphine.

136. The pharmaceutical composition of claim 37, wherein the drug is oxycodone.

137. The pharmaceutical composition of claim 37, wherein the drug is hydromorphone.

138. The pharmaceutical composition of claim 37, wherein the drug is oxymorphone.

* * * * *

UNITED STATES PATENT AND TRADEMARK OFFICE
CERTIFICATE OF CORRECTION

PATENT NO. : 10,314,788 B2
APPLICATION NO. : 13/058757
DATED : June 11, 2019
INVENTOR(S) : Manish S. Shah and Ray J. Difalco Page 1 of 3

It is certified that error appears in the above-identified patent and that said Letters Patent is hereby corrected as shown below:

In the Claims

Column 18, Line 27 (Claim 1), replace "quarternary" with -- quaternary --

Column 18, Line 37 (Claim 1), replace "wherein the" with -- wherein when the --

Column 18, Line 65 (Claim 3), replace "quarternary" with -- quaternary --

Column 19, Line 8 (Claim 3), replace "wherein the" with -- wherein when the --

Column 19, Line 30 (Claim 4), replace "quarternary" with -- quaternary --

Column 19, Line 40 (Claim 4), replace "wherein the" with -- wherein when the --

Column 19, Line 66 (Claim 6), replace "quarternary" with -- quaternary --

Column 20, Line 9 (Claim 6), replace "wherein the" with -- wherein when the --

Column 20, Line 37 (Claim 8), replace "quarternary" with -- quaternary --

Column 20, Line 47 (Claim 8), replace "wherein the" with -- wherein when the --

Column 21, Line 9 (Claim 10), replace "quarternary" with -- quaternary --

Column 21, Line 19 (Claim 10), replace "wherein the" with -- wherein when the --

Column 21, Line 46 (Claim 12), replace "qua ternary" with -- quaternary --

Column 21, Line 56 (Claim 12), replace "wherein the" with -- wherein when the --

Signed and Sealed this
Thirtieth Day of July, 2019

Andrei Iancu
*Director of the United States Patent and Trademark Office*

CERTIFICATE OF CORRECTION (continued)
U.S. Pat. No. 10,314,788 B2

Column 22, Line 23 (Claim 14), replace "quarternary" with -- quaternary --

Column 22, Line 33 (Claim 14), replace "wherein the" with -- wherein when the --

Column 22, Line 65 (Claim 16), replace "quarternary" with -- quaternary --

Column 23, Line 8 (Claim 16), replace "wherein the" with -- wherein when the --

Column 23, Line 38 (Claim 18), replace "quarternary" with -- quaternary --

Column 23, Line 48 (Claim 18), replace "wherein the" with -- wherein when the --

Column 24, Line 9 (Claim 20), replace "quarternary" with -- quaternary --

Column 24, Line 19 (Claim 20), replace "wherein the" with -- wherein when the --

Column 24, Line 47 (Claim 22), replace "quarternary" with -- quaternary --

Column 24, Line 57 (Claim 22), replace "wherein the" with -- wherein when the --

Column 25, Line 12 (Claim 23), replace "quarternary" with -- quaternary --

Column 25, Line 22 (Claim 23), replace "wherein the" with -- wherein when the --

Column 25, Line 48 (Claim 25), replace "quarternary" with -- quaternary --

Column 25, Line 58 (Claim 25), replace "wherein the" with -- wherein when the --

Column 26, Line 20 (Claim 27), replace "quarternary" with -- quaternary --

Column 26, Line 30 (Claim 27), replace "wherein the" with -- wherein when the --

Column 26, Line 59 (Claim 29), replace "quarternary" with -- quaternary --

Column 27, Line 3 (Claim 29), replace "wherein the" with -- wherein when the --

Column 27, Line 30 (Claim 31), replace "quarternary" with -- quaternary --

Column 27, Line 40 (Claim 31), replace "wherein the" with -- wherein when the --

Column 28, Line 5 (Claim 33), replace "quarternary" with -- quaternary --

Column 28, Line 15 (Claim 33), replace "wherein the" with -- wherein when the --

Column 28, Line 47 (Claim 35), replace "quarternary" with -- quaternary --

CERTIFICATE OF CORRECTION (continued)
U.S. Pat. No. 10,314,788 B2

Column 28, Line 57 (Claim 35), replace "wherein the" with -- wherein when the --

Column 29, Line 22 (Claim 37), replace "quarternary" with -- quaternary --

Column 29, Line 32 (Claim 37), replace "wherein the" with -- wherein when the --

Column 30, Line 66 (Claim 80), replace "he" with -- the --